United States Patent
Lim et al.

(10) Patent No.: US 8,076,532 B2
(45) Date of Patent: Dec. 13, 2011

(54) TRANSGENIC MOUSE DEFECTIVE IN WW45 FUNCTION AND USE IN SCREENING COMPOUNDS FOR ANTI-TUNOUR ACTIVITY

(75) Inventors: Dae-Sik Lim, Daejeon (KR); Joo-Hyeon Lee, Daejeon (KR); Tae-Shin Kim, Daejeon (KR); Tae-Hong Yang, Daejeon (KR); Bon-Kyoung Koo, Daejeon (KR); Sang-Phil Oh, Daejeon (KR); Kwang-Pyo Lee, Daejeon (KR); Hyun-Jung Oh, Daejeon (KR); Sang-Hee Lee, Daejeon (KR); Young-Yun Kong, Daejeon (KR); Jin-Man Kim, Daejeon (KR)

(73) Assignee: Korea Advanced Institute of Science and Technology, Guseong-Dong, Yuseong-Gu, Daejeon (KR)

( * ) Notice: Subject to any disclaimer, the term of this patent is extended or adjusted under 35 U.S.C. 154(b) by 197 days.

(21) Appl. No.: 12/412,496

(22) Filed: Mar. 27, 2009

(65) Prior Publication Data

US 2009/0312251 A1  Dec. 17, 2009

(30) Foreign Application Priority Data

Jun. 17, 2008  (KR) ........................ 10-2008-0056758

(51) Int. Cl.
*A01K 67/027* (2006.01)
*A01K 67/00* (2006.01)
*A01K 67/033* (2006.01)
*G01N 33/00* (2006.01)

(52) U.S. Cl. .................... 800/18; 800/8; 800/9; 800/10; 800/3; 424/9.2

(58) Field of Classification Search ..................... 800/18
See application file for complete search history.

(56) References Cited

OTHER PUBLICATIONS

Denning and Priddle, 2003, Reproduction, 126:1-11.*
Smith, Jour Biotechnolo, 2002, 99:1-22.*
Rami L. Aqeilan et al., "WW Domain-Cintaining Proteins, WWOX and YAP, compete for Interaction with ErbB-4 and Modulate Its Transcriptional Function", Cancer Research vol. 65 pp. 6764-6772 (Aug. 1, 2005).
Qi Zeng et al., "The Emerging Role of the Hippo Pathway in Cell Contact Inhibition, Organ Size Control, and Cancer Development in Mammals", Cancer Cell vol. 13 pp. 188-192 (Mar. 11, 2008).
Joo-Hyeon Lee, et al., A crucial role of WW45 in developing epithelial tissues in the mouse, The EMBO Journal, (2008) 27, 1231-1242.

* cited by examiner

*Primary Examiner* — Valarie Bertoglio
(74) *Attorney, Agent, or Firm* — Lexyoume IP Group, PLLC.

(57) ABSTRACT

Mechanisms regulating cell proliferation stop and differentiation initiation during the development stage of mammalian embryo, and the proteins involved therein, are presented. Differentiation regulators, methods of regulating differentiation, transgenic organisms with loss of expression of the differentiation regulator, and methods of preparing the transgenic organisms, are provided.

5 Claims, 34 Drawing Sheets

Yki (SEQ ID NO: 19)  LAIHHSRARSSPASLQQ

YAP (SEQ ID NO: 20)  LTPQHVRAHSSPASLQL

RXXS motif

TRANSGENIC MOUSE DEFECTIVE IN WW45 FUNCTION AND USE IN SCREENING COMPOUNDS FOR ANTI-TUNOUR ACTIVITY

CROSS-REFERENCE TO RELATED APPLICATION

This application claims priority to and the benefit of Korean Patent Application No. 10-2008-0056758 filed in the Korean Intellectual Property Office on Jun. 17, 2008, the entire content of which is incorporated herein by reference.

BACKGROUND OF THE INVENTION (a) Field of the Invention

Mechanisms regulating cell proliferation stop and differentiation initiation during the development stage of mammalian embryo, and the proteins involved therein, are provided. More specifically, differentiation regulators, methods of regulating differentiation, transgenic organisms with loss of expression of the differentiation regulator, and methods of preparing the transgenic organisms, are provided.

(b) Description of the Related Art

Homeostasis of regenerative epithelial tissues such as skin and intestine is maintained through a tightly balanced process of proliferation and terminal differentiation. During normal epithelial development, proliferating progenitor cells, often referred to as transiently amplifying (TA) cells, actively divide a limited number of times before they undergo cell-cycle exit and terminally differentiate into postmitotic cells. Cancer can develop as a result of inappropriate proliferation of progenitor cells accompanied by a partial or complete loss of differentiation. Therefore, understanding the signaling networks that control cell-cycle exit and terminal differentiation in epithelial tissues will provide insights into the mechanisms underlying tumorigenesis.

A new signaling network, known as the "Hippo pathway" in *Drosophila*, seems to be a key developmental program in controlling proliferation and apoptosis for proper organ development in *Drosophila*. The Ste-20 family kinase Hippo, WW adaptor protein Salvador and NDR kinase Warts are key components of the Hippo pathway that restricts cell proliferation and promotes apoptosis in differentiating epithelial cells by regulating expression of cyclin E and Diap1. The Hippo kinase phosphorylates and activates the Warts kinase, and this process is facilitated by the scaffolding protein Salvador or Mats. Warts, together with Mats, then phosphorylates and inhibits the transcription coactivator Yorkie. Expanded, Merlin and Fat, all of which localize to the plasma membrane, function upstream of the Hippo pathway. In flies, mutations of these factors lead to increased cell proliferation and decreased cell death.

The phenotypes of flies with mutations in the Hippo pathway can be rescued with their respective human counterparts, indicating that the Hippo pathway may play an analogous role as a global regulator of epithelial tissue development in mammals. Several reports on each mammalian component of the Hippo pathway have shown that the pathway is involved in cell death and cell-cycle regulation. MST1/2 kinases (Hippo homologs) were originally reported to be involved in apoptosis with caspase-3-mediated proteolytic activation. LATS1/2 (Warts homologs) have been implicated in the regulation of cell-cycle progression, apoptosis, mitotic exit and cytokinesis. YAP (a Yorkie homolog) has been shown to be involved in apoptosis by interacting with p73. Although mutation of WW45 (a Salvador homolog) has been reported in several cancer cell lines, little is known about the functional significance of WW45 in mammals. So far, only limited biochemical interactions have been reported, including the phosphorylation of LATS1/2 by MST1/2, the association of WW45 with MST1/2 and LATS1/2, binding of LATS1 to MOB1 (a MATS homolog) and formation of a complex comprising RASSF1A, MST2, WW45 and LATS1.

The Hippo pathway has also been implicated in mammalian tumorigenesis. Mice lacking LATS1 develop some types of tumor, and hWW45 and Mats are mutated in several cancer cell lines. NF2, the human ortholog of Merlin, is a tumor-suppressor gene, mutations of which lead to neurofibromatosis. YAP is overexpressed in mammalian cancers and transgenic mice overexpressing YAP have an increased liver size and dysplasia with expanded undifferentiated progenitor cells in the intestine. Of the Hippo pathway proteins, only LATS1-, LATS2-, NF2-, and YAP-null mice have been generated; however, these mice are either early embryonic lethal or fail to recapitulate defects seen in the respective *Drosophila* mutants. Therefore, compared with *Drosophila*, much less is known about the physiological function of the Hippo pathway in mammalian epithelial development. Furthermore, the molecular mechanisms by which this pathway is regulated during development are not fully understood in mammals.

SUMMARY OF THE INVENTION

An embodiment of the present invention provides a novel use of a WW45 protein and/or a phosphorylated YAP in regulating differentiation in a mammal.

Another embodiment provides a method of regulating differentiation in a mammal by regulating the expression of a WW45 protein and/or the phosphorylation of a Yes-associated protein (YAP).

Another embodiment provides a differentiation regulating agent in mammal including one or more selected from the group consisting of a WW45 protein, a polynucleotide encoding the WW45 protein, a phosphorylated YAP, and a polynucleotide encoding the YAP, as an active ingredient.

Another embodiment provides a non-human transgenic organism whose whole or part of a ww45 protein coding gene is deleted, whereby tumor is induced.

Another embodiment provides a method of preparing a non-human transgenic organism by deleting a whole or part of a ww45 protein coding gene.

Another embodiment provides a method of screening an anti-tumor agent using the non-human transgenic organism.

Still another embodiment provides a method of screening a differentiation regulating agent by measuring the expression level of WW45 protein in a mammalian cell.

DETAILED DESCRIPTION OF THE EMBODIMENTS

The present inventors generated mice lacking WW45, which is the unique Sav homolog, to examine the role of the Hippo pathway in mammals, and revealed that mutant embryos displayed unchecked proliferation and defects in terminal differentiation of epithelial cells, to complete the present invention. The present inventors also revealed the molecular mechanism by which MST1 signaling is spatiotemporally regulated to allow cell-cycle exit and activation of terminal differentiation in epithelial cells.

Based on the above findings, mechanisms regulating cell proliferation stop and differentiation initiation during the development stage of mammalian embryo, and the proteins involved therein, are presented. More specifically, differentiation regulators, methods of regulating differentiation, transgenic organisms with loss of expression of the differentiation regulator, and methods of preparing the transgenic organisms, are provided.

One object of the present invention is to reveal the processes of cell-cycle exit (cell proliferation stop) and terminal differentiation, and provide a novel use of a WW45 protein involved in the processes.

Therefore, an embodiment provides a method of regulating differentiation in a mammal by regulating the expression of a WW45 protein, the phosphorylation of a Yes-associated protein (YAP), or the movement of phosphorylated YAP from nucleus to cytoplasm, and a differentiation regulating agent in a mammal including one or more selected from the group consisting of a WW45 protein, a polynucleotide encoding the WW45 protein, a phosphorylated YAP, and a polynucleotide encoding the YAP, as an active ingredient.

Figure 16A:
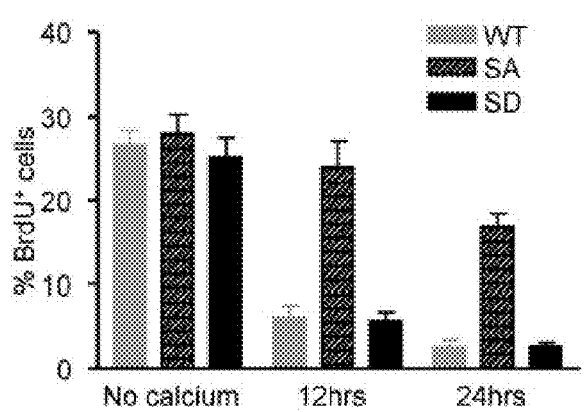
FIGS. 16a to 16f show effects of phosphorylation of YAP serine 127 on epithelium differentiation, wherein 16a shows the percentage of proliferative cells labeled with BrdU under differentiation conditions, 16b shows that YAP-SA-infected cells fail to differentiate in response to differentiation stimuli, 16c shows subcellular localization of YAP, YAP SA and YAP SD in response to differentiation stimuli, 16d shows the percentage of BrdU-positive cells in WW45-deficient keratinocytes infected with the indicated genes under differentiation conditions, 16e shows the result of western-blot analysis for lysates obtained from 16d with the indicated antibodies, and 16f schematically shows a proposed model for the role of WW45 in developing epithelial tissues FIGS. 17a and 17b expansion of progenitor cells and loss of differentiated cells in WW45−/− epithelium, wherein 17a shows representative H&E and anti-K1 stained sections of epidermis from control and mutant embryos at the indicated developmental stages, and 17b shows representative H&E-stained sections of intestine from control and mutant embryos at the indicated developmental stages (Scale bar: 100 μm).
Figure 16B:
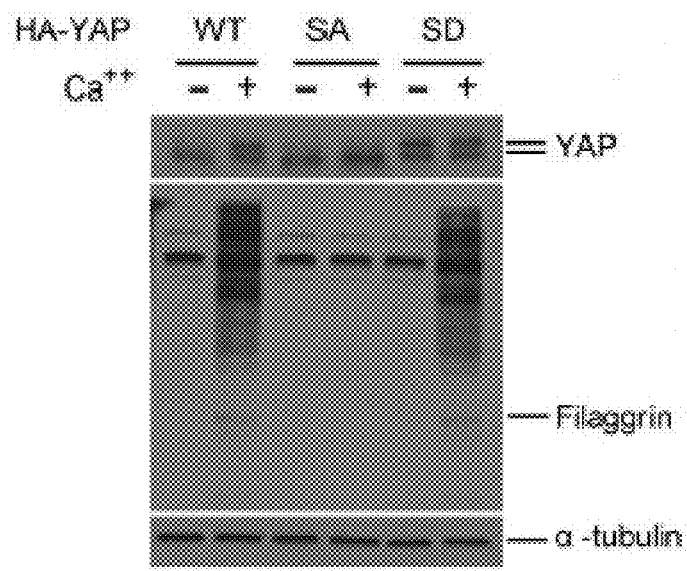
Figure 16C:
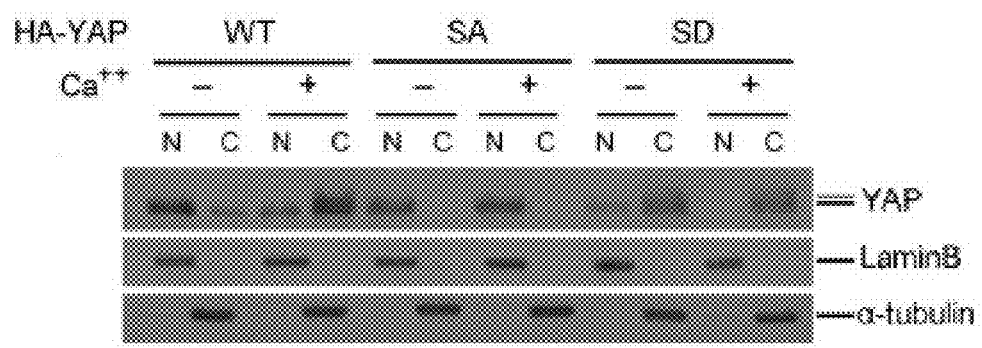
Figure 16D:
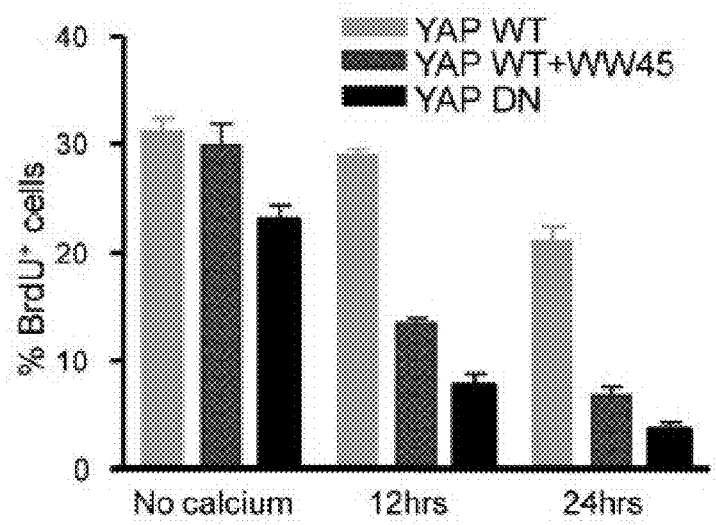
Figure 16E:
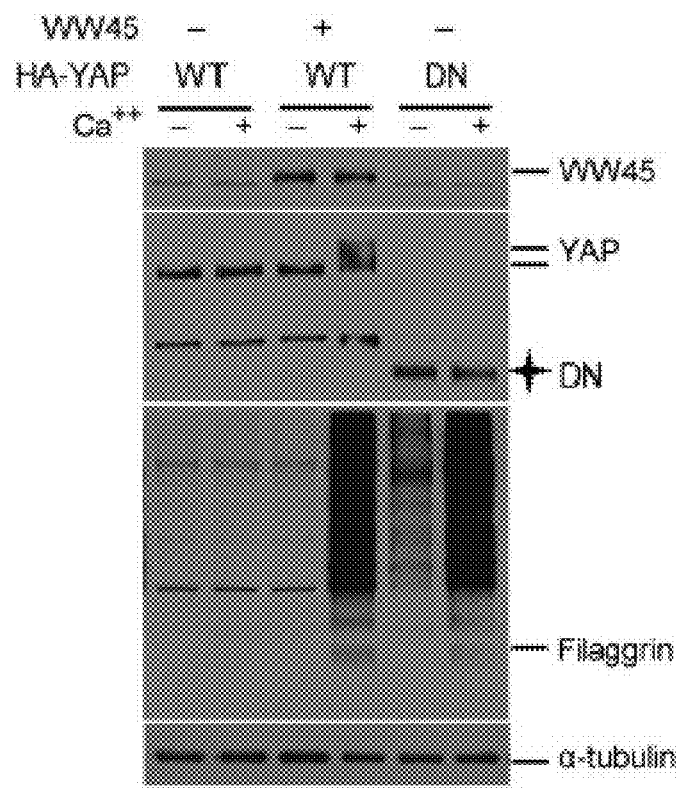
Figure 16F:
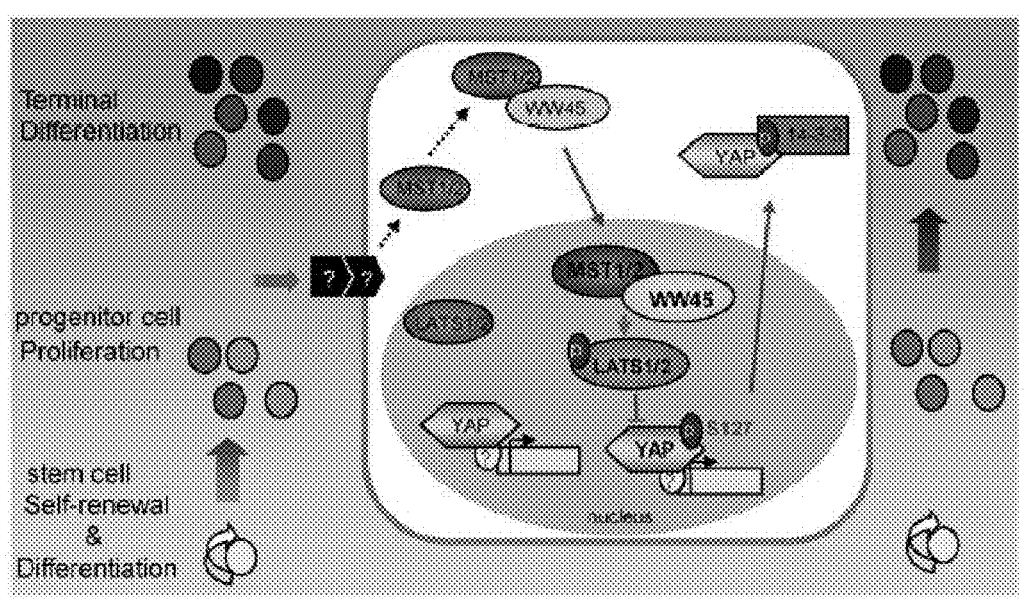

In embodiments of the present invention, the role of WW45 protein in cell-cycle exit (cell proliferation stop) and differentiation initiation is examined from the finding that in mice lacking WW45, cells proliferation is continued, and differentiation cannot be initiated. Based on the findings of the present invention including the above, the processes of terminating cell proliferation and initiating differentiation may be as follows: The WW45 protein is located in cytoplasm during cell proliferation, and when differentiation conditions are given, the WW45 protein forms a complex with MST1/2 that is present in cytoplasm, to move into nucleus. The MST1/2-WW45 complex that moves into nucleus stimulates LATS1/2 that is present in nucleus, thereby phosphorylating YAP that is present in nucleus. The phosphorylated YAP moves from nucleus to cytoplasm, and binds to 14-3-3 protein, resulting in terminating cell proliferation and initiating differentiation. The above processes are schematically shown in FIG. 16*f.*

The WW45 protein may be any WW45 proteins present in mammals. For example, the WW45 protein may be one or more selected from the group consisting of a human WW45 protein (e.g., SEQ ID NO: 1, GenBank Accession No.: NP_068590.1), and rodent WW proteins such as a mouse (*Mus musculus*) WW45 protein (e.g., SEQ ID NO: 2, GenBank Accession No.: NP_071311), a rat (*Rattus norvegicus*) WW45 protein (e.g., SEQ ID NO: 3, GenBank Accession No.: NP_001091050), and the like, but not be limited thereto. The WW45 protein may form a complex with MST1/2 in cytoplasm and moves into nucleus.

In embodiments of the present invention, it is revealed that the termination of cell proliferation and initiation of differentiation occur when phosphorylted YAP moves from nucleus to cytoplasm, indicating that the movement of the phosphorylted YAP from nucleus to cytoplasm plays an important role in initiating cell differentiation. The YAP may be any YAP present in mammals. For example, the YAP may be one or more selected from the group consisting of a human YAP (e.g., SEQ ID NO: 4, GenBank Accession No.: NP_006097.1), and rodent YABs such as a mouse (*Mus musculus*) YAP (e.g., SEQ ID NO: 5, GenBank Accession No.: NP_033560.1), a rat (*Rattus norvegicus*) YAP (e.g., SEQ ID NO: 6, GenBank Accession No.: NP_001029174), and the like, but not be limited thereto. The phosphorylated site of YAP that is phosphorylated by LATS1/2 which is stimulated by the MST1/2-WW45 protein complex may be $127^{th}$ amino acid, serine, (hereinafter, 'serine 127'), among other phosphorylation sites. The YAP where serine 127 is phosphorylated may move to cytoplasm, and binds with 14-3-3 protein, allowing cell proliferation terminated, and cell differentiation initiated.

As used herein, the term 'differentiation regulating agent' means any material that is capable of regulating (promoting or inhibiting) any process of a series of processes involved in terminating cell proliferation and initiating cell differentiation.

The method or agent for regulating differentiation according to the present invention may be applied to cells, tissues or organs of any mammal including human. Preferably, the mammal may be human or rodent, and the cells, tissues or organs may be epithelial cells or tissues of skin or internal organs, for example, epithelial cells of intestine, lung, kidney, thymus, pancreas, and the like, and/or epidermal cells of skin, more specifically, keratinocytes. The time to apply the method or agent for regulating differentiation according to the present invention may be the time when the cell proliferation is terminated and the cell differentiation is initiated, which may be determined depending on the cells, tissues or organs to which the method or agent is applied. For example, the time to apply the method or agent may be the period between around E14.5 to P1. The method or agent for regulating differentiation according to the present invention may regulate the differentiation from epithelial progenitor cells to epithelial cells.

Another embodiment of the present invention provides a non-human transgenic organism with inhibited expression or functional loss of the WW5 protein. In a concrete embodiment, the non-human transgenic organism may be a transgenic animal with the receipt number of KCTC11343BP.

Another embodiment of the present invention provides a method of preparing a non-human transgenic organism with inhibited expression or functional loss of the WW5 protein. The method may include the steps of:

1) preparing a recombinant gene where whole or part of WW45 protein coding gene is deleted or substituted, or a recombinant expression vector (gene targeting vector) comprising the recombinant gene and a promoter operably linked the recombinant gene;

2) transfecting an embryo, fertilized ovum, or embryonic stem cell (ES cell) of a non-human mammal with the prepared recombinant gene or recombinant expression vector; and 3) culturing the transfected embryo, fertilized ovum, or ES cell, to obtain a transgenic animal (gene targeting animal), and a tissue or organ of the transgenic animal.

The transfecting step may be performed by any conventionally known method that is used for preparation of a transgenic animal using ES cell. For example, the method of preparing a transgenic mouse may be performed by: selectively injecting the recombinant gene or recombinant expression vector into a ES cell; injecting the resulted ES cell into blastocyst (E3.5), to prepare a chimeric mouse through a surrogate mother; mating the prepared chimeric mouse with a normal mouse, to obtain a heteromouse where only a copy of the WW45 coding gene is deleted; and then, mating the heteromice, to construct a transgenic mouse where two copies of the WW45 coding gene is deleted.

The transgenic animal according to the present invention may be characterized in that the WW45 protein is operated so as not to be expressed or to have functional loss, whereby apoptosis is inhibited, and thus, cell proliferation is not terminated and cell differentiation is not initiated, resulting in inducing tumor. Therefore, the transgenic animal may be useful as a animal model with tumor.

As used herein, the term 'animal model' refers to any animal that has a specific disease similar to human disease, thereby being used as an experimental subject for revealing the pathogens, and checking the pathological condition. The animal to be used as an animal model may be one that is easily prepared, has repeatability and reproducibility, and is expected that the similar result to human can be obtainable. In addition, in the animal, it is preferable that pathogen and progress of diseases are similar to human. Therefore, the animal may be preferably one belonging to mammals like human, where the internal structure of the body such as internal organs, immune system, body temperature, and the like, are similar to human, and diseases such as hypertension, cancer, immunodeficiency, and the like, can be induced.

From this point of view, the transgenic animal may be produced from any mammal, for example, a horse, a sheep, a pig, a goat, a camel, an antelope, a dog, or a rodent such as a mouse, a rat, a guinea pig, hamster, and the like, wherein a rodent such as a mouse, a rat, a guinea pig, hamster, and the like may be preferable. In particular, the mouse has been most widely used in studying human diseases because of several advantages such as a small size, a superior fertility, an easy feeding management, a strong resistance to diseases, a genetic uniformity, development of various species, and a possibility to produce an animal that has a similar disease or pathological condition.

The induction of tumor in the transgenic animal may occur at one or more tissues or organs selected from the group consisting of skin epithelium, intestine epithelium, kidney epithelium, lung epithelium, thymus epithelium, pancreas epithelium, and the like. Therefore, the transgenic animal may be useful as a tumor-induced animal model, where the tumor may be one or more selected from a liver cancer, a lung cancer, a blood tumor, a skin cancer, a gastric cancer, a large intestine cancer, a small intestine tumor, a kidney cancer, and the like.

In an embodiment, the inhibition of WW45 protein expression and functional loss may be performed by any conventional transfection technique using a recombinant gene where whole or part of WW45 protein coding gene is deleted or substituted, or a recombinant expression vector prepared by inserting the recombinant gene into a proper expression vector. For example, the inhibition of WW45 protein expression and functional loss may be achieved by deleting or substituting whole or part of WW45 protein coding gene, where the part of WW45 protein coding gene may be a region containing at least SARAH domain.

The WW45 protein coding gene may be a WW45 protein coding gene of mammal including human. For example, the WW45 protein coding gene may be one or more selected from the group consisting of human WW45 protein coding gene (the region from $339^{th}$ to $1490^{th}$ positions of SEQ ID NO: 7 (GenBank Accession No. NM_021818.2), mouse (*Mus musculus*) WW45 protein coding gene (the region from $236^{th}$ to $1396^{th}$ positions of SEQ ID NO: 8 (GenBank Accession No. NM_022028.2), rat (*Rattus norvegicus*) WW45 protein coding gene (the region from $172^{nd}$ to $1335^{th}$ positions of SEQ ID NO: 9 (GenBank Accession No. NM_001097581), and the like, but not be limited thereto.

The deletion or substitution of whole or part of the WW45 protein coding gene may include any operations to prevent a complete expression of WW45 protein, or make the expressed WW45 protein incapable of forming a complex with MST1/2 to fail to move into nucleus. Therefore, in embodiment, the deletion of part of WW45 protein coding gene may mean a deletion of at least SARAH domain that plays a role to interact with MST1.

The identical sequences of SARAH domain of WW45 are as follows:

treating a sample cell with a candidate compound; and
measuring the level of WW45 protein expression, MST1/2 activation, LATS1/2 phosphorylation, or YAP phosphorylation, in the cell.

The sample cell may be any cell obtained from any mammal including human, and for example, epithelial cells of skin, intestine, and the like, more specifically, epidermal cells, keratinocytes, crypt cells, and the like. The levels of WW45 protein expression, MST1/2 activation, LATS1/2 phosphorylation, and YAP phosphorylation may be determined by any conventional quantitative or analyzing method of protein known to the relevant art.

The method of screening a differentiation regulating agent may be a method of screening a differentiation promoting agent characterized by determining a candidate compound as a differentiation promoting agent when the level of WW45 protein expression, MST1/2 activation, LATS1/2 phosphorylation, and/or YAP phosphorylation is increased after treating the candidate compound. Alternatively, the method of screening a differentiation regulating agent may be a method of screening a differentiation inhibiting agent characterized by determining a candidate compound as a differentiation inhibiting agent when the level of WW45 protein expression, MST1/2 activation, LATS1/2 phosphorylation, and/or YAP phosphorylation is decreased after treating the candidate compound.

Embodiments of the present invention provide novel insights into the role of WW45 in mammalian epithelial tissue development. WW45 protein is a key regulator of the MST1 signaling pathway, which promotes cell-cycle exit and terminal differentiation in developing epithelial tissues. It is found that ablation of WW45 leads to hyperproliferation accompanied by immature differentiation in epithelial cells of the skin and intestine (FIGS. 3 and 4), and that this phenotype results from re-entry of differentiating cells to the cell cycle rather than intrinsic acceleration of proliferation (FIG. 8).

Figure 17A:
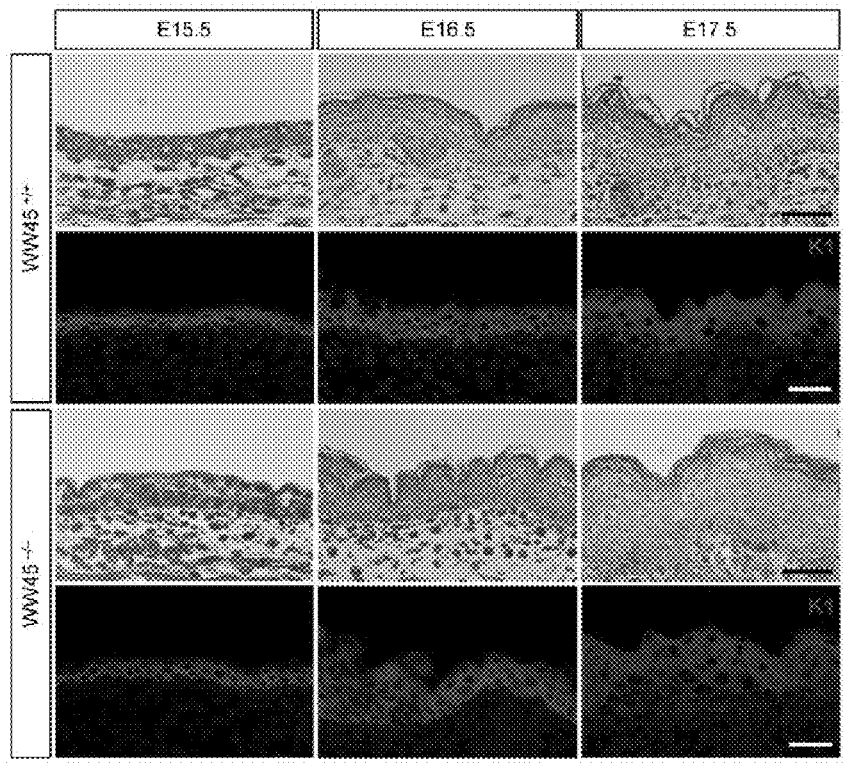
Figure 17B:
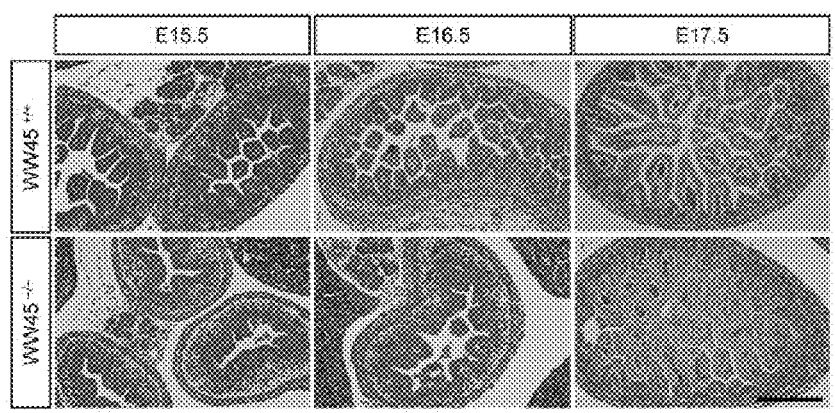
Figure 18:
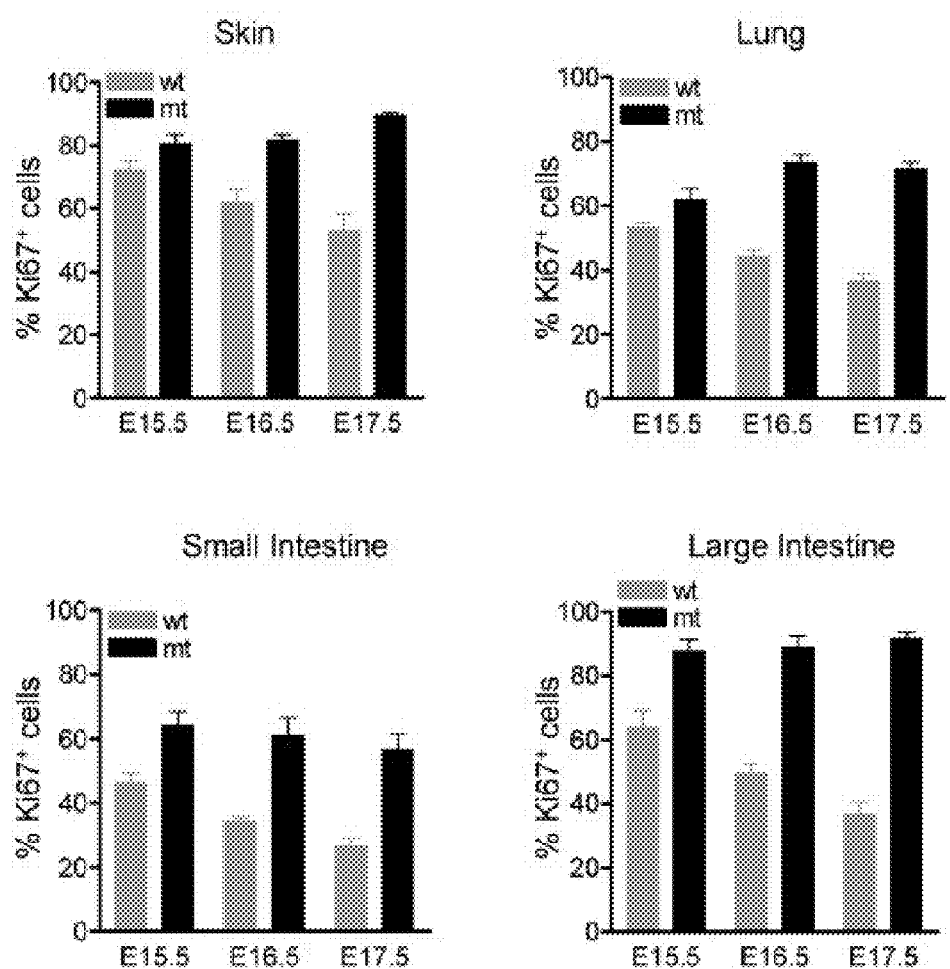
FIG. 18 shows the number of Ki67-positive cells (average number per 1.0-mm2 area) in wild-type and mutant epithelia at the indicated developmental stages (Data represent triplicate independent experiments ±SD).

This conclusion is strongly supported by our observations that WW45-deficient primary keratinocytes cannot be efficiently induced to exit the cell cycle in response to differentiation signals such as $Ca^{2+}$, TGF- or LiCl, and that increased proliferation rates were detected from E15.5 onwards, which is the onset of terminal differentiation events in the epithelium (FIGS. 8, 17 and 18). The Hippo pathway has been implicated in the restriction of proliferation and promotion of apoptosis in epithelial cells, but there is little evidence that this pathway is involved in terminal differentiation in *Drosophila*. Interestingly, the mouse MST1 signaling pathway seems to have a role in terminal differentiation in the developing epithelial tissues.

Previous studies with *Drosophila* have identified several genes and their interactions in the Hippo pathway; however, the intracellular signaling of spatiotemporal regulation during epithelial differentiation remains unclear. The inventors determine the underlying mechanism by which components of the MST1 signaling pathway spatiotemporally regulate cell-cycle exit for epithelial differentiation in mammals.

The inventors show that as-yet-unknown differentiation signals specifically activate the MST1 kinase, which then dynamically localizes to the nucleus and activates LATS1/2, and that wild-type WW45 is required for this process. Activated LATS1/2 then phosphorylates serine 127 of YAP, and this phosphorylated YAP localizes to the cytoplasm where it is inactivated (FIG. 16*d*). Recently, it has been reported that serine 127 of YAP is the main phosphorylation site in the Hippo pathway and its phosphorylation results in its cytoplasmic translocation; overexpression of YAP in mice induces a severe dysplasia accompanied by expansion of multipotent undifferentiated progenitor cells in the skin and intestine.

These phenotypes are quite similar to those seen in the WW45-null embryos. Here, the inventors have shown that phosphorylation of serine 127 of YAP by LATS1/2 in MST signaling occurs during epithelial differentiation. Based on the observations and the phenotypic similarities between YAP transgenic and WW45-null mice, the inventors propose a hypothesis that, during formation of mature epithelial tissues in mammals, the MST1 pathway is activated by differentiation signals and determines when precursor cells stop dividing and terminally differentiate, and that WW45 may be central to this process (FIG. 16*f*).

Interestingly, transgenic mice overexpressing YAP S127A in the liver displayed enlarged livers, supporting the hypothesis that Hippo signaling regulates mammalian organ size. However, no organs of increased size were seen in WW45$^{-/-}$ embryos, which could be due to placental defects or another genetic compensation. Thus, tissue-specific or conditional knockout experiments in mice are required for further clarification of the role of the MST1 pathway in regulation of organ size in mammals.

Figure 19:
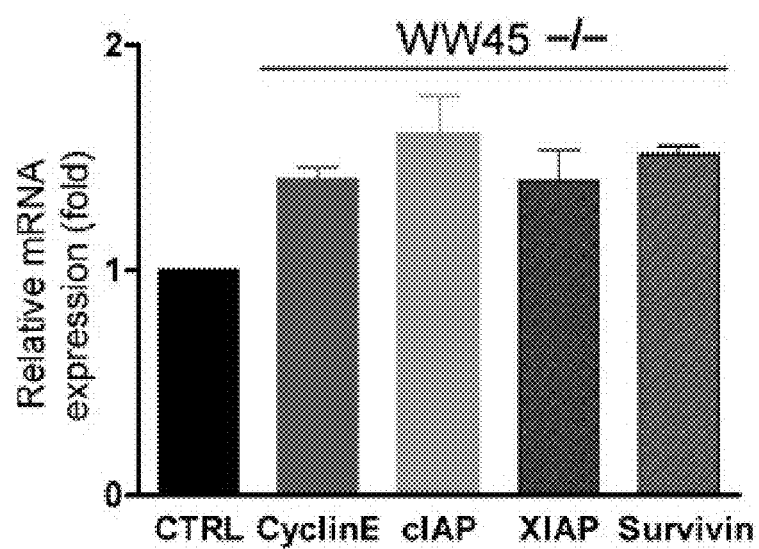
FIG. 19 shows the analysis results from quantitative RT-PCR for RNA isolated from wild-type and mutant epidermis (Data represent triplicate independent experiments ±SD).

Recent studies in *Drosophila* have indicated that, together with cyclin E, Diap1 and bantam may be an additional target of Yorkie. However, unlike in *Drosophila*, no direct target genes were identified in the MST1 pathway. Of interest, quantitative RT-PCR revealed that, although slightly increased, expression levels of cyclin E, cIAP, XIAP and survivin were not significantly upregulated in WW45$^{-/-}$ cells, indicating that other targets of YAP control developmental homeostasis in mammalian epithelial tissues (FIG. 19). Based on the observation that YAP DN is sufficient to rescue the cell-cycle exit and differentiation of WW45$^{-/-}$ cells, identification of the downstream targets or mediators of YAP will provide important insights into how YAP could control both cell-cycle exit and terminal differentiation.

The inventors also found that WW45 deficiency led to disruption of contact inhibition of proliferation, as is also seen with loss of LATS2 and NF2. WW45 is also likely to participate in the contact inhibition signaling pathway. Loss of contact inhibition might be associated with the hyperplasia observed in epithelial tissues of WW45$^{-/-}$ embryos. Recently, inactivation of YAP in the Hippo pathway has been shown to contribute to cell contact inhibition and tissue growth. Thus, further studies should investigate whether defects in contact inhibition in WW45$^{-/-}$ cells are due to a failure of YAP inactivation.

Perturbations in MST1 signaling lead to inappropriate proliferation and expansion of cell compartments, which in turn lead to increased risks of cancer-associated mutations. Several results support the importance of the Hippo pathway in mammalian tumorigenesis. Loss of expression of LATS1 and LATS2, and mutation of hWW45 and Mats have been reported in cancer cell lines. Mice with mutations in LATS1 or NF2 develop tumors, and YAP transcription is increased in the mouse tumor model.

Moreover, YAP can transform immortalized mammary epithelial cells in vitro and transgenic mice overexpressing YAP develop liver cancers or intestinal dysplasia with loss of differentiated cell types. In addition to these reports, the inventors strikingly revealed that dysfunction of a single gene, WW45, affects most developing epithelial tissues, and induces characteristics of a precancerous state: uncontrolled proliferation, partial loss of epithelial polarity and block of terminal differentiation. However, no such phenotypes have been reported in mice lacking LATS1, LATS2 and NF2.

Multiple homologs of the fly Hippo pathway exist in mammals; hence, there may be functional redundancy of these proteins. However, WW45 is the only mammalian homolog of the Sav scaffold protein in the Hippo pathway, and loss of WW45 led to marked phenotypic changes in many epithelial tissues. Importantly, it is found that, during a 14-month observation period, 22% of WW45-heterozygous mice developed some type of tumor including osteosarcoma and hepatoma. Therefore, future studies should investigate how the heterozygous status of WW45 initiates tumorigenesis and the molecular characteristics of developed tumors in these mice. Finally, according to embodiments of the present invention, the WW45-knockout embryo or WW45-heterozygous mice could be a suitable model for tumorigenesis studies of the MST1 pathway.

Here, a novel use of WW45 protein in termination of proliferation (cell cycle exit) and initiation of differentiation, which is expected to be useful in searching a differentiation regulators, and preparing a WW45-knockout or WW45-heterozygous transgenic animal for various studies.

EXAMPLES

The present invention is further explained in more detail with reference to the following examples. These examples, however, should not be interpreted as limiting the scope of the present invention in any manner.

Example 1

Generation of WW45 Null Mice

WW45 gene targeting vector was injected into ES cells by electroporation, and WW45 gene-deficient ES clones were examined by Southern blotting. The WW45 gene-deficient targeting ES clones were injected into blastocyst, to prepare a chimeric mouse.

Figure 1A:
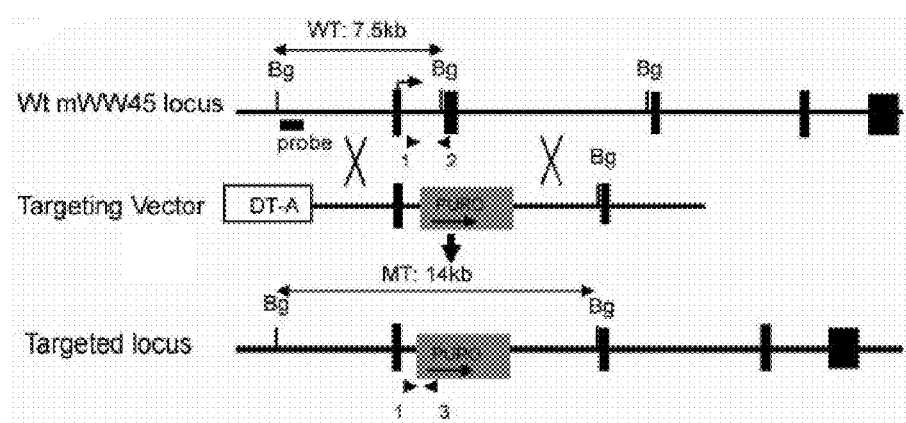
FIGS. 1*a* to 1*d* show targeted disruption of the WW45 gene by homologous recombination, wherein 1*a* is a schematic representation of the WW45 targeting strategy, showing the mouse WW45 genomic locus, targeting vectors and targeted locus, 1*b* shows the result of southern-blot analysis of genomic DNA digested with the restriction enzyme Bgl II using the 5'-probe, and PCR genotype analysis of embryos, 1*c* shows a macroscopic appearance of wild-type and mutant embryos at E17.5 (top), and growth curves of wild-type (+/+) and mutant (−/−) WW45 embryos (bottom), and 1*d* shows Hematoxylin and Eosin (H&E)-stained sections of placentas from E17.5 wild-type and mutant embryos.

More specifically, a WW45$^{-/-}$ mouse was generated using standard ES cell (R1) homologous recombination and blastocyst injection techniques (Lim et al., 1996; Lee et al., 2006). A WW45 targeting vector was prepared by subcloning left arm (obtained from 6338 bp containing exon1 using EcoR I restriction enzyme (New England Biolabs, NEB)) and right arm (obtained from 3443 bp using BamH I restriction enzyme (NEB)) into pGK-Puro vector (obtained from pBluscript II KS(+) vector (Stratagene) as a backbone) using 129SvJ mouse BAC clone (obtained from Korea Research Institute of Bioscience & Biotechnology) (FIG. 1a). More specifically, puromycin resistance gene, which is a positive selection marker, was cloned between left arm and right arm, to replace exon2, and diphtheria toxin-A (DT-A), which is a negative selection marker, was cloned into Not I site, to produce a pGK-Puro-WW45 gene targeting vector.

The produced WW45 gene targeting vector was deposited with the Korean Collection for Type Cultures (KCTC) at Yuseong-gu, Daejeon, Korea, on Jun. 12, 2008, and allotted receipt number KCTC11342BP.

WW45$^{-/-}$ mice were generated by injecting the WW45 gene targeting vector into a mouse ES cell (BayGenomics) through electroporation to a targeted ES cell clone, and injecting the ES cell clone into C57BL/6 blastocysts (E3.5, purchased from Jackson Lab) to generate germ-line-transmitting chimeric mice. Mice and ES cells were genotyped by polymerase chain reaction (PCR) assays. The primers and conditions used in the PCR are as follows:

```
WW45-L:   5'-TGACCATGTGTCCAGCCTTA-3',   (SEQ ID NO: 13)

WW45-R:   5'-CGAATGGATGCTGCATATTG-3',   (SEQ ID NO: 14)

pGK-3:    5'-GCACGAGACTAGTGAGACGTGCTAC-3'. (SEQ ID NO: 15)
```

Conditions: denature at 94° C. for 30 seconds; annealing at 60° C. for 45 seconds; elongation at 72° C. for 1 minute, 30 cycle.

Using Applied biosystems Geneamp PCR system 2700 PCR apparatus.

Example 2

Histological Analysis

The chimeric mouse produced in Example 1 was mated with a normal mouse (purchased from C57BL/06, Jackson Lab) to produce WW45 hetero mouse where only one copy of WW45 gene is deleted. It was confirmed by PCR that the embryo obtained by mating the resulted WW45 hetero mice is mutants where the WW45 gene is deleted. The resulted embryo of the transgenic animal was deposited to the Korean Collection for Type Cultures (KCTC) at Yuseong-gu, Daejeon, Korea, on Jun. 12, 2008 and allotted receipt number KCTC11343BP.

The embryos were fixed in 4% paraformaldehyde overnight at 4° C., embedded in paraffin and sectioned to the size of 4 μm. The sections (4 μm) were stained with hematoxylin and eosin (H&E) or subjected to immunohistochemical analysis. Immunohistochemical analysis was performed using standard protocols (Koo et al., 2007) with antibodies against PECAM-1 (BD), laminin (Abcam), BrdU (Sigma), E-cadherin (BD), β-catenin (BD), Ki67 (Novocastra), anti-filaggrin (Covance), loricrin (Covance), K10 (Covance), K14 (Covance), K1 (Covance), iFABP (gift from Dr J. I. Gordon), chromogranin A (Immunostar), YAP (Cell Signaling, Santa Cruz), and p-YAP (Cell Signaling). Peroxidase levels were assessed using the EnVision®+ Dual Link System-HRP (DAB+) (DakoCytomation). Intestinal goblet cells were stained with Alcian blue to detect mucin. The TUNEL assay (koo et al., 2005) was performed using a commercial staining kit (Roche). BrdU incorporation experiments were performed by injecting pregnant females intraperitoneally with BrdU (Sigma) at a concentration of 100 μg/g body weight. At 1 hour, 2 hours, or 24 hours after injection, embryos were dissected and fixed for immunohistochemical analysis.

Example 3

Barrier Function Assays

At E17.5, the embryos were rinsed in phosphate-buffered saline (PBS) and immersed in acidic X-gal mix (100 mM phosphate buffer at pH4.3, 3 mM $K_3Fe(CN)_6$, 3 mM $K_4Fe(CN)_6$, 2 mM $MgCl_2$, 1 mg/mL X-gal), then incubated for 8 hours at 37° C. in the dark (Hardman et al., 1998).

Example 4

Electron Microscopy

Electron-microscopy analysis of the obtained tissue samples was performed according to standard protocols. Briefly, the samples were fixed with 3% glutaraldehyde for 2 hours and then washed with 0.1 M cacodylate buffer containing 0.1% $CaCl_2$. The Samples were then post-fixed with 1% $OsO_4$ in 0.1 M cacodylate buffer (pH 7.2) containing 0.1% $CaCl_2$ for 2 hours at 4° C. After dehydration in graded alcohol concentrations, the cells were embedded in Spurr's epoxy resin. After polymerization of the resin at 70° C. for 36 hours, serial sections were cut and mounted on formvar-coated slot grids. The sections were stained with 4% uranyl acetate for 10 minutes and with lead citrate for 7 minutes. A Tecnai G2 Spirit Twin transmission electron microscope (FEI Company, USA) and a JEM ARM 1300S high-voltage electron microscope (JEOL, Japan) were used.

Example 5

Quantitative Real-Time PCR

Total RNAs from the tissue samples were extracted using Trizol (Gibco). cDNA was generated using SS II RT kit (Invitrogen). Expression of genes indicated in the text was measured by real-time qRT-PCR (Bio-rad iQ5 multicolor real-time PCR detection system), and normalized to GAPDH (glyceraldehyde-3-phosphate dehydrogenase) expression levels.

Example 6

Plasmid Construction

Human cDNAs for WW45, MST1, LATS1/2 and YAP (WW45: GenBank Accession No. NP_068590.1, MST1: GenBank Accession No. NP_006273.1, LATS1: GenBank Accession No. NP_004681.1, LATS2: GenBank Accession No. NP_055387.2, YAP: GenBank Accession No. NP_006097.1) were cloned into pDK-Flag2 or pCMV-HA, which had been modified from pcDNA3.1 or pcDNA3 (Invitrogen), respectively, where the pDK-Flag2 or pCMV-HA was generated by inserting Flag or HA tagging using the pcDNA3.1 or pcDNA3 (Invitrogen) as backbone. Site-directed PCR mutagenesis was used to introduce the missense changes S61A, S109A, S127A, T328A and S347A into the YAP sequence. The S127A-nuclear-localizing form with a deletion of the C-terminal TA-domain of YAP was generated and used for YAP-DN mutant form. The cDNAs for YAP and its serine to alanine (SA) mutant form were cloned into pET-15b (Novagen) to generate recombinant hexahistidine (His6)-tagged YAP and SA proteins, respectively.

Example 7

Generation of Antibodies

Rabbit polyclonal antibodies to MST1 were prepared with purified recombinant hexahistidine (His6)-tagged MST1 (K59R, KAIST) as an antigen and then affinity purified and used for immunostaining. Rabbit polyclonal antibodies to WW45 (Rb Ctr#1) were generated by injecting rabbits with a keyhole-limpet-hemocyanin-conjugated peptide corresponding to the 14 C-terminal amino acids of mouse WW45 (RKQRQQWYAQQHGK; SEQ ID NO: 16). Specific antibodies were affinity purified with the appropriate antigens (RKQRQQWYAQQHGK).

Example 8

Primary Keratinocyte Cultures

Keratinocytes isolated from embryos at E17.5 were cultured in PCT Epidermal Keratinocyte Medium (Chemicon), where the embryos were prepared by removing a womb from a pregnant mouse generated by mating ww45 hetero mice at $17.5^{th}$ day by caesarean section, then collecting embryos therefrom, removing placenta and amnion from each embryo, conforming genotype of each embryo by the removed amnion, and then selecting embryos that correspond to each genotype. Differentiation was induced by adding $CaCl_2$ to a concentration of 1.2 mM, TGF-β to a concentration of 1 ng/ml (R&D) and LiCl to concentration of 10 mM to the culture medium. BrdU (Sigma) was added to the medium (10 μM) and cells were incubated for 1 hour before being fixed and processed for immunostaining. For growth-curve analysis, 3×105 cells from passage 2 were plated in six-well plates, and the total numbers of cells were counted daily. Transfections were performed with Effectene reagents (Qiagen) or with polyethyleneimine (Sigma). Retroviral infections were performed according to standard protocols (Song et al., 2004).

Example 9

Immunoprecipitation, Subcellular Fractionation, Western-Blot Analysis and Immunofluorescence Primary keratinocytes were lysed in 25 mM Tris-HCl (pH 7.4), 150 mM NaCl, 1 mM EDTA, 1 mM $MgCl_2$, 0.2% TritonX-100, 0.3% NP-40, protease inhibitors (Roche Protease inhibitor cocktails) and phosphatase inhibitors (NaF, sodium fluoride), where the primary keratinocytes were prepared by extracting epithelium from the E17.5 embryo's skin, treating dispase thereto on the embryo's skin, separating epithelial layer, and then isolating single cell from the epithelial layer. The resulted cell lysates were incubated for 2 hours at 4° C. with antibodies (antibodies against LATS1/2: Bethyl_Laboratories, INC; and antibodies against MST1: prepared in Example 7), and then with protein A/G plus-agarose beads to be subjected to immunoprecipitation. The resulted immunoprecipitates were subjected to Western-blot analysis or the immunoprecipitation (IP)-kinase assay. Separation of nuclear and cytoplasmic extracts was performed using NE-PER® Nuclear (PIERCE) and Cytoplasmic Extraction Reagents (PIERCE). Western-blot analysis was performed using antibodies against YAP (Cell Signaling), p-YAP (Cell Signaling), MST1 (Cell Signaling), p-MST1 (Cell Signaling), LATS1 (Bethyl Laboratories, INC), LATS2 (Bethyl Laboratories, INC), hemagglutinin (HA, Covance), filaggrin (Covance), laminin B (Santa Cruz), α-tubulin (Chemicon), Flag (Sigma) and WW45 (Example 7). For immunostaining analysis, keratinocytes were fixed in absolute methanol at −20° C. for 10 minutes and then exposed consecutively to primary and secondary antibodies. Slides were mounted with 4',6-diamidino-2-phenylindole (DAPI) and imaged.

Example 10

In-Vitro Kinase Assay

Immunoprecipitated HA-LATS1/2-WT or -KD were incubated for 30 minutes at 30° C. with purified His-YAP-WT or His-YAP-SA in kinase buffer (25 mM HEPES pH 7.4, 50 mM NaCl, 5 mM $MgCl_2$, 5 mM $MnCl_2$, 5 mM β-glycerophosphate and 1 mM dithiothreitol) supplemented with 10 μM adenosine 5'triphosphate (ATP) and 2 μCi [γ-32P] ATP. The reaction mixtures were analyzed by SDS-PAGE and autoradiography to detect 32P-labeled YAP.

Experimental Example 1

Retarded Growth and Perinatal Lethality of the WW45-Deficient Mice

To identify the role of WW45 in vivo, WW45 mutant mice were generated using embryonic-stem (ES)-cell technology (see Example 1). The targeted mutation of the example was characterized by replacing a 2.4-kb genomic region containing WW45 exon 2 (at 330$^{th}$ to 773$^{rd}$ positions of SEQ ID NO: 8 (GenBank Accession No. NM_ 022028): atctcatgcc ttcattcatt cggcacggtc caacaattcc cagacggact gacctctgtcttccagattc aagtgctact gctttctcag cttctggaga tggtgtagtt tcaagaaacca gagtttcct gagaactgca attcaaagga cacctcatga agtaatgaga agagaaagccacagactgtc tgcccttct taccttgtca ggagcctagc agatgtccct cgagagtgtggctcatcaca gtcattttg acagaagtta actttgctgt tgagaatgga gactctggctcccgatactt cttctcagat aacttttttg atggacagag aaggcggcca cttggagatcgtgcacaaga agattacaga tattatgaat acaaccatga tctcttccag aggatgccacagagtcaggg gaggcacact tcag) with a puromycin cassette (Lim et al., 1996; Lee et al., 2006), leading to premature stop in WW45.

Electroporation, puromycin positive selection and diphtheria toxin negative selection were performed, and a 5' external flanking probe was prepared by PCR on genomic DNA using two primers, SP-1 and SP-r.

The nucleotide sequences of the primers are as follows:

```
                                    (SEQ ID NO: 17)
Sp-1:    5'-CCT AGA CCC TTT CAA CAA GCA-3'

(SEQ ID NO: 18)
Sp-r:    5'-TGC TAT CAC TCA TCG GGA TT-3'
```

After screening by Southern blotting (Combi H12, FinePCR) using the prepared probe, the targeted clone was identified, and transmitted through the germline after crossing the chimeric mice with C57BL/6 mice (purchased from Jackson Lab) (FIG. 1a).

FIG. 1 shows targeted disruption of the WW45 gene by homologous recombination, wherein FIG. 1a is a schematic representation of the WW45 targeting strategy, showing the mouse WW45 genomic locus, targeting vectors and targeted locus. Exon 2 was replaced with a puro cassette, and diphtheria toxin A was used for negative selection (Lee et al., 2006). Five exons are indicated by black boxes. Also indicated are the 5'-external probe for Southern hybridization of genomic DNA, predicted sizes of hybridizing fragments with restriction sites, and primer pairs for PCR. Arrowheads represent primers (see Example 1) used for genotyping of the WT (1 and 2) or MT (1 and 3) alleles, and Bg indicates Bgl II restriction site.

The absence of WW45 protein was confirmed by fractioning liquid protein obtained from mutant mouse embryonic fibroblasts (MEFs) by electrophoresis and then Western blotting (FIG. 1B), indicating a null allele in mutant mice.

Figure 1B:
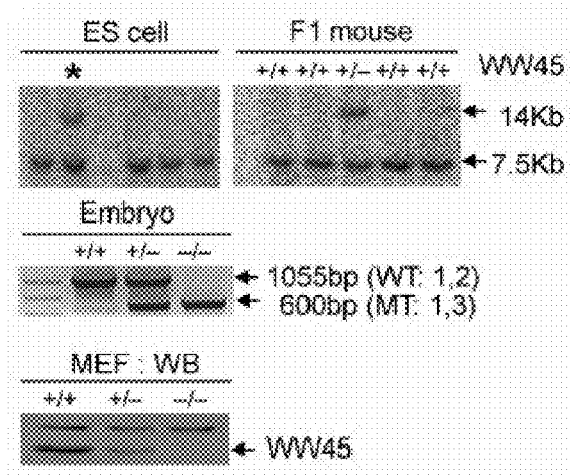

FIG. 1b shows the result of Southern-blot analysis of genomic DNA digested with the restriction enzyme Bgl II using the 5'-probe, and PCR genotype analysis of embryos (see Example 1). Western-blot analysis (WB) shows the presence of WW45 in cultured primary fibroblasts. Arrow indicates bands of WW45.

The Southern blotting shown in FIG. 1b was performed by extracting genomic DNA from embryonic stem cells and transgenic mice, treating a restriction enzyme, and performing electrophoresis on 0.9% agarose gel, to transfer onto nylon membrane. The DNA attached nylon membrane was hybridized with P$^{32}$-CTP-labeled 5'-external probe, and washed, and the obtained band was imaged.

Heterozygous mice were born healthy and fertile, and developed normally. However, only 3 dwarf homozygotes were found among 954 littermates generated from heterozygous intercrosses, indicating that most of the null mice were embryonic lethal. Viable WW45−/− embryos were found at embryonic days 17.5 (E17.5) and E18.5. The obtained results are shown in Table 1.

TABLE 1

Genotypes of progeny from WW45 heterozygous intercrosses

| Age (dpc) | No. per genotype | | | |
|---|---|---|---|---|
| | +/+ | +/− | −/− | Total |
| 17.5 | 168 | 352 | 85 | 605 |
| 18.0 | 17 | 34 | 6 | 57 |
| 18.5 | 22 | 46 | 6 | 72 |
| 19.0 | 4 | 2 | 0 | 6 |
| Neonates | 350 | 601 | 3 | 954 |

Figure 1C:
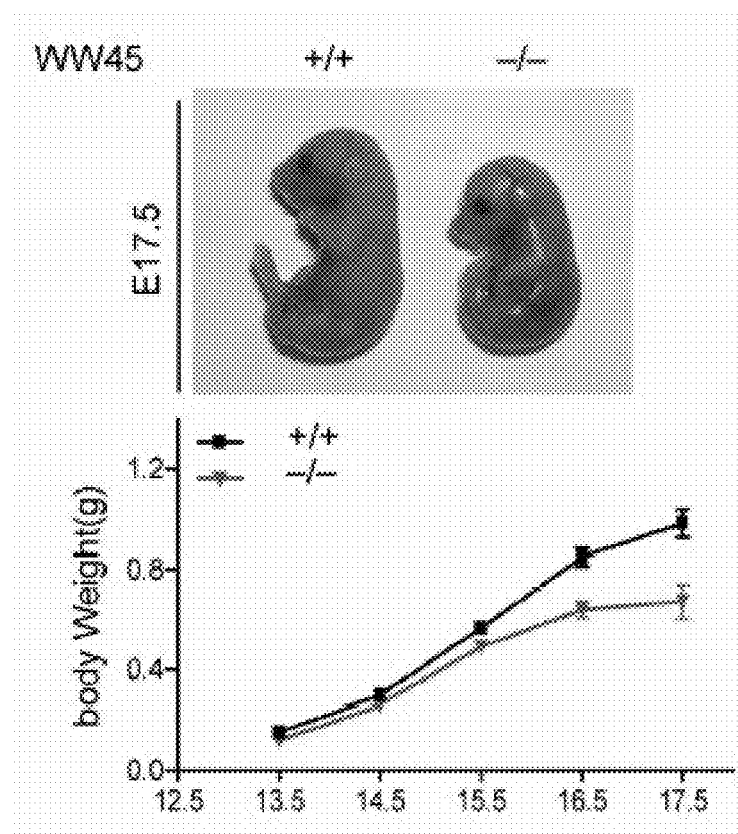

WW45−/− embryos up to E11.5 were morphologically indistinguishable from their control littermates. However, from about E13.5 onwards, WW45−/− embryos were slightly smaller than the controls, indicating a slower gain in body weight (FIG. 1c). The upper part of FIG. 3c shows a macroscopic appearance of wild-type and mutant embryos at E17.5, and the bottom part shows growth curves of wild-type (+/+) and mutant (−/−) WW45 embryos, indicating growth retardation of mutant (−/−) WW45 embryos. Despite the growth retardation, no consistent overt defects that would cause the embryonic lethality of mutants were observed.

Figure 1D:
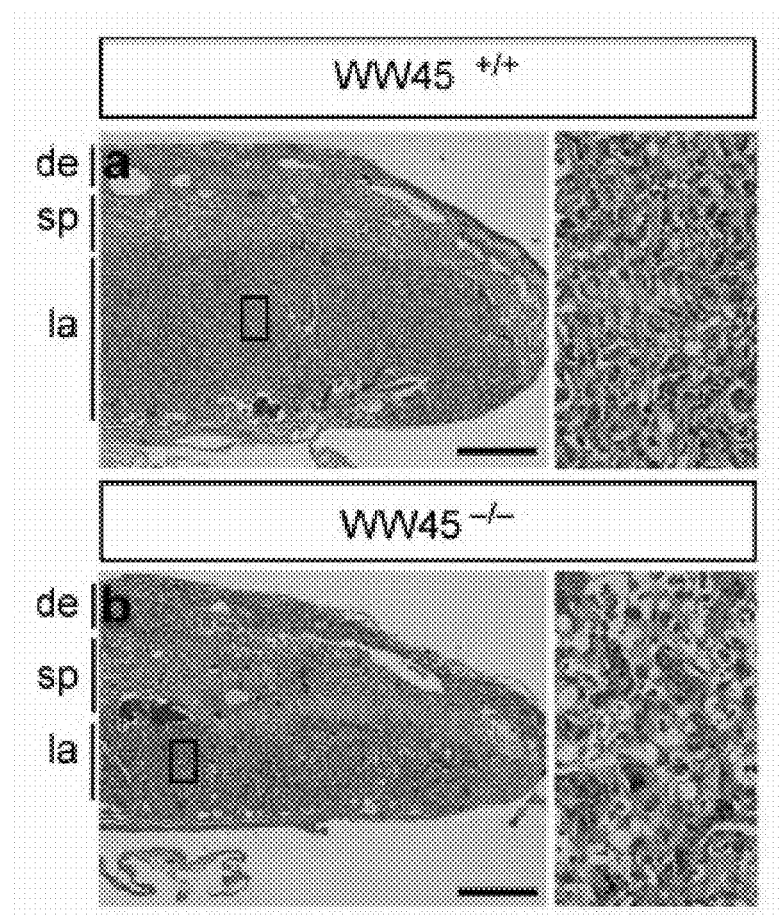

This result prompted the inventors to examine placentas from mutants and their littermates. Vascular invasion normally proceeded with increasing development of the labyrinth layer in wild-type placentas. By contrast, mutant placentas displayed immature development with poor growth and vascularization of the labyrinth layers (FIG. 1d). FIG. 1d shows hematoxylin and eosin (H&E)-stained sections of placentas from E17.5 wild-type and mutant embryos. It was found that the major layers had defective maturations with reduced and disordered vasculature in mutant placentas (de, decidua; sp, spongiotrophoblast layer; 1a, labyrinth layer. Scale bar: 500 µm). Boxed regions are shown at high magnification.

Figure 2:
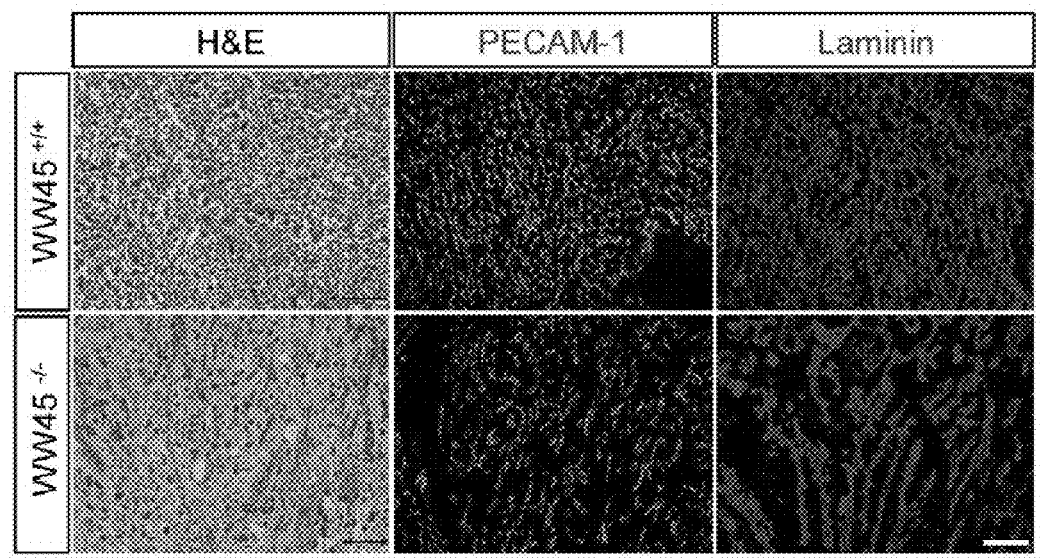
FIG. 2 shows defective angiogenesis in WW45−/− placenta at E17.5 (Scale bar: 100 μm).

Defective intermingling of fetal and maternal vessels was confirmed by staining with anti-PECAM1 and anti-Laminin according to Example 2, and the obtained result was shown in FIG. 2. FIG. 2 is picture showing defective vascularization of WW45$^{−/−}$ placenta at E17.5. As shown in FIG. 2, Extraembryonic vascular defects were confirmed by immunohistochemistry analysis with antibodies against PECAM-1 and laminin. Scale bar: 100 µm.

In conclusion, the malfunctional labyrinth layer may affect the growth and viability of WW45−/− embryos.

Experimental Example 2

Hyperplasia and Immature Differentiation of Epithelial Cells in the WW45-Deficient Embryos Previous *Drosophila* studies have proposed important roles for SAV1 in regulation of proliferation and apoptosis in epithelial tissues. Thus, histological analyses of WW45−/− embryos were performed at various embryonic stages. Interestingly, hyperproliferation of epithelial cells was clearly observed in the skin and intestine (FIGS. 2 and 3) and other organs (FIG. 5) of the WW45−/− embryos at E17.5. The experiment was performed according to the method of Example 2.

The inventors first characterized skin development in these WW45$^{-/-}$ mice. FIG. 3 shows hyperproliferation and immature differentiation in WW45$^{-/-}$ epidermis at E17.5. Dividing keratinocytes are normally restricted to the basal layer of wild-type epidermis, and as cells exit from the cell cycle, these keratinocytes move outward and differentiate to form the spinous layers, the granular layers, and the dead enucleated stratum corneum layers at the skin surface (FIG. 3a-a).

Figure 3A:
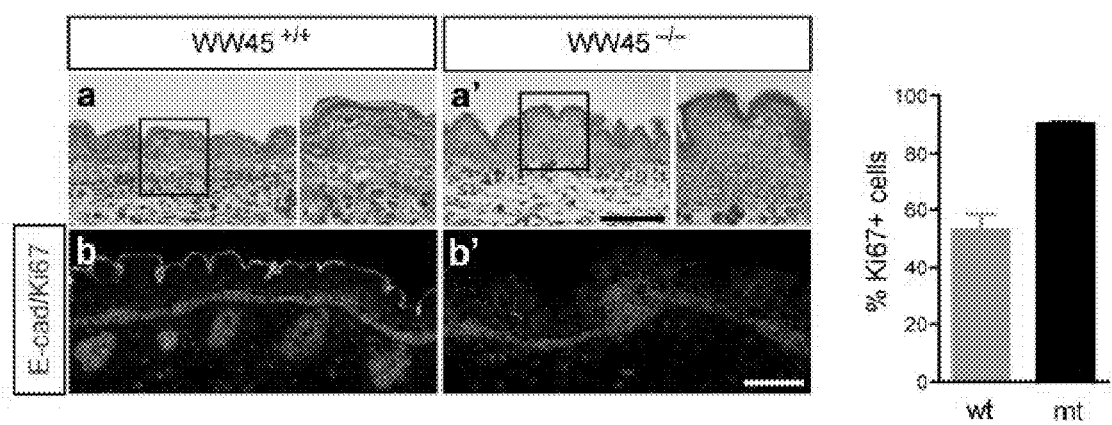
FIGS. 3a to 3c show hyperproliferation and immature differentiation in WW45$^{-/-}$ epidermis at E17.5, wherein 3a shows the result of histological analysis of Hematoxylin and Eosin (H&E)-stained sections of wild-type (a) and mutant (a') epidermis, 3b shows the differentiation marker expression in skin of wild-type or mutant embryos, and 3c shows the result of electron-microscopy analysis of the wild-type (upper panel) and mutant (lower panel) epidermis (Scale bar: 100 μm in (A) and (B), 2 μm in (C)).
Figure 3B:
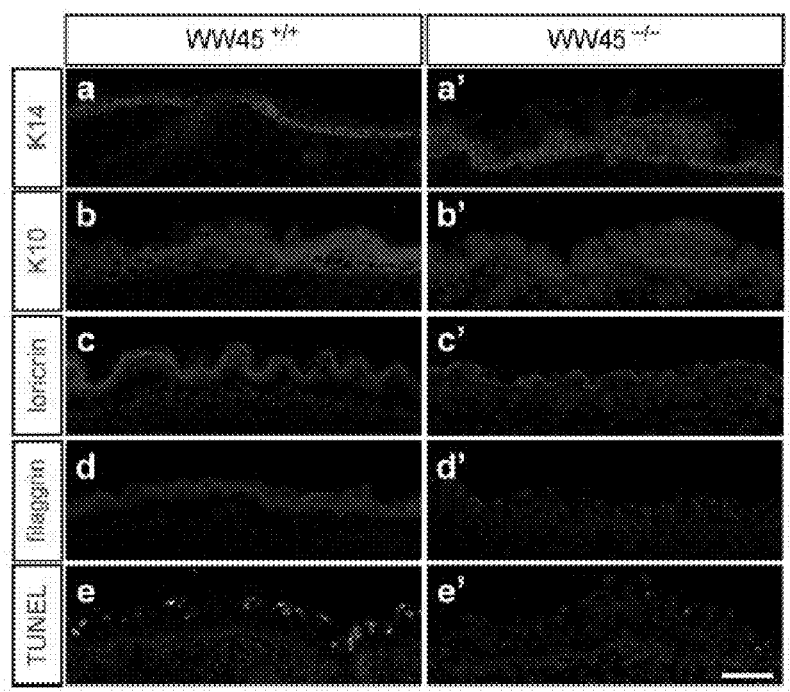
Figure 3C:
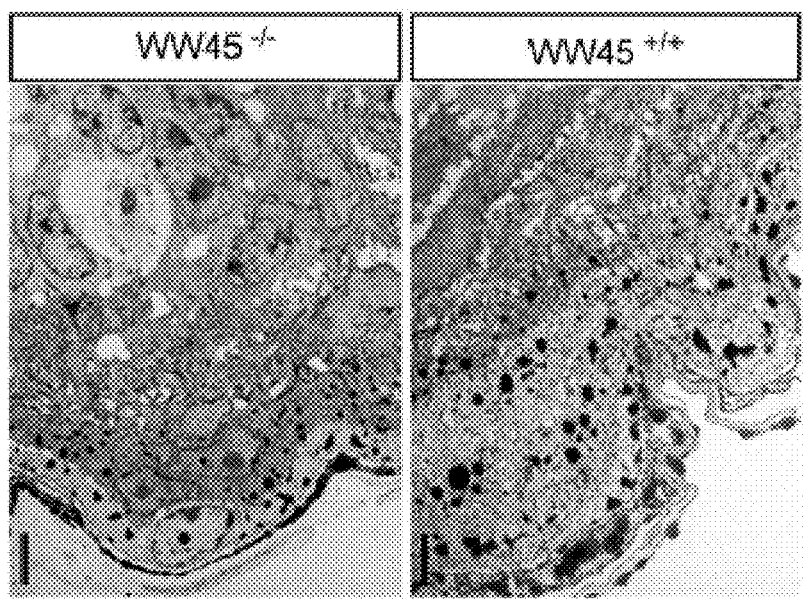

By contrast, the epidermis of null embryos had a more dense basal layer and the expanded suprabasal layers were less differentiated, with reduced enucleation and compaction of the developing granular cells (FIG. 3a-a'). Development of hair follicles was rarely seen, and only small premature hair follicles were seen in null embryos at this stage. Co-immunostaining for E-cadherin and Ki67 revealed that the skin of mutant embryos contained increased numbers of proliferative epithelial cells, compared with wild-type embryos (FIG. 3a-b, b'). Almost all the basal cells and several suprabasal cells expressed Ki67 in the mutant epidermis, whereas proliferation was restricted to the basal layer in the wild-type epidermis.

FIG. 3a shows the result of histological analysis of Hematoxylin and Eosin (H&E)-stained sections of wild-type (a) and mutant (a') epidermis. Evaluation of cellular proliferation was conducted by co-immunohistochemistry analysis with anti-Ki67 and anti-E-cadherin (b, b'). The increased numbers of Ki67-positive cells, including in multiple cell layers, were found in the mutant epidermis. Quantitation of the percentage of proliferating cells per 1-mm² area in mutant versus control epithelium from three independent experiments (±SD). Boxed regions are shown at high magnification in the right panel of each genotype. wt, wild-type; mt, mutant.

TUNEL (terminal deoxynucleotidyl transferase biotindUTP nick-end labeling)-positive cells were also shown in epidermis from wild-type embryos, but not in epidermis from null embryos (FIG. 3b-e, e'). FIG. 3b shows differentiation marker expression in skin of wild-type or mutant embryos. Immunohistochemistry analysis was performed with antibodies against K14, K10, loricrin and filaggrin, in addition to TUNEL staining for analysis of apoptosis. 4',6-diamidino-2-phenylindole (DAPI)-stained nuclei are shown in blue. The lack of stratification and differentiation and the increased numbers of progenitor cells in the mutant epidermis were found. Thus, increased proliferation in the suprabasal layer and repressed apoptosis of terminally differentiated keratinocytes contribute to hyperplasia in the epidermis of mutant embryos.

Epithelia of WW45$^{-/-}$ embryos were hyperproliferative but did not seem to undergo normal differentiation; therefore, the inventors investigated whether epithelial differentiation was delayed and/or defective in mutant epithelia using a panel of antibodies against proteins that are expressed at defined stages of differentiation. Keratin 14 was normally expressed in one or two layers of basal cells in wild-type embryos, whereas it was strongly expressed in the multilayered basal cells in WW45$^{-/-}$ embryos (FIG. 3b-a, a').

Figure 4A:
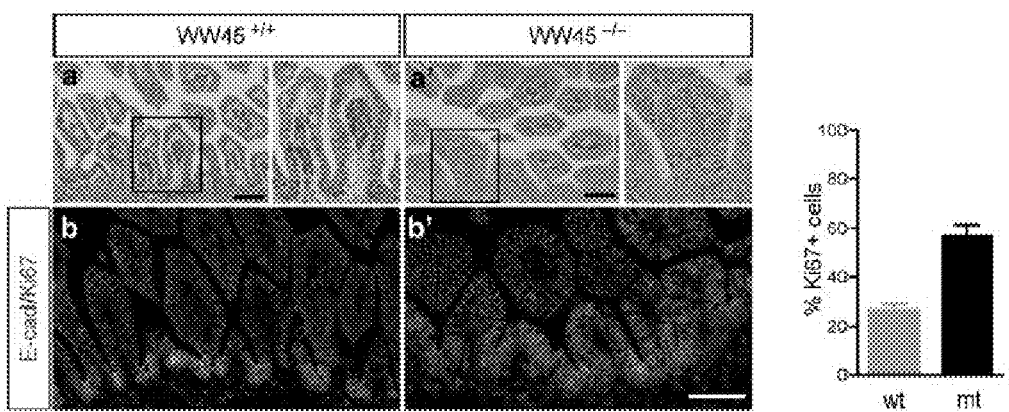
FIGS. 4a to 4c show hyperplasia and immature differentiation of WW45−/− intestinal epithelium at E17.5, wherein 4a shows H&E-stained sections of wild-type (a) and mutant (a') intestine, 4b shows the differentiation marker expression in the intestine of wild-type or mutant embryos, and 4c shows the result of electron-microscopy analysis of the wild-type (upper panel) and mutant (lower panel) intestines (Scale bar: 100 μm in (A) and (B), 2 μm in (C)).
Figure 4B:
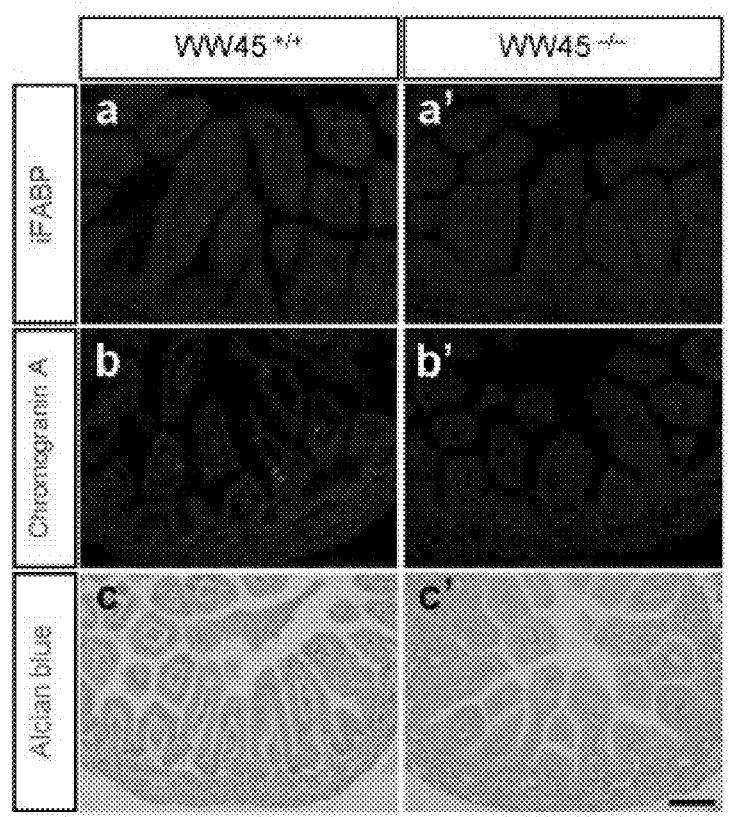
Figure 4C:
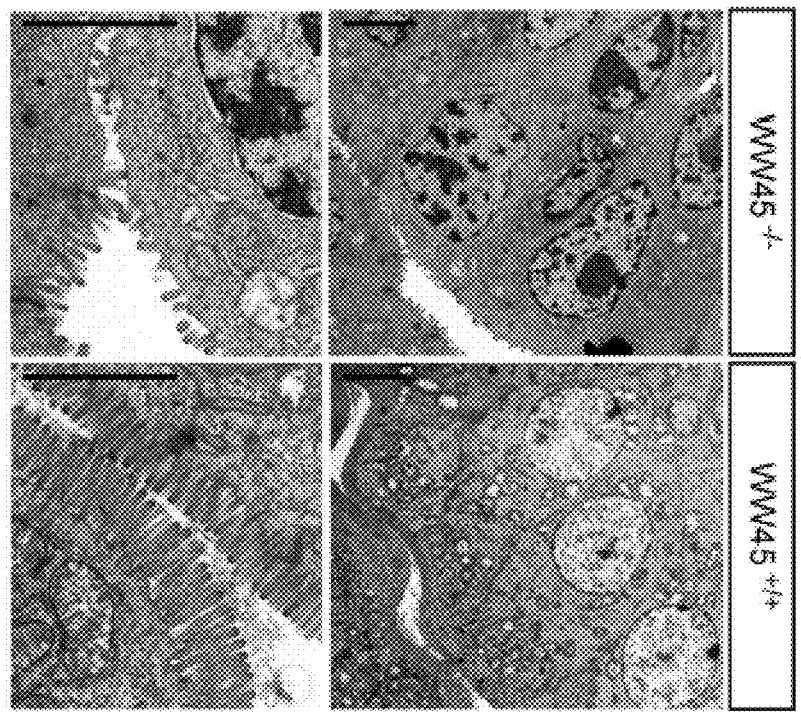

FIG. 4 shows hyperplasia and immature differentiation of WW45$^{-/-}$ intestinal epithelium at E17.5, wherein FIG. 4a shows H&E-stained sections of wild-type (a) and mutant (a') intestine. The results from immunohistochemistry analysis with anti-Ki67 and anti-E-cadherin were indicated (b, b'). The increased numbers of Ki67-positive cells, including in multiple cell layers, were observed in the mutant epithelium. Quantitation of the percentage of proliferating cells per 1-mm² area in mutant versus control epithelium from three independent experiments (±SD). Boxed regions are shown at high magnification in the right panel of each genotype. wt, wild-type; mt, mutant. FIG. 4b shows differentiation marker expression in the intestine of wild-type or mutant embryos. Immunohistochemistry analysis was performed with antibodies against iFABP and chromogranin A, in addition to Alcian-blue staining. The significant reductions in levels of terminal differentiating cells, goblet cells and entero-endocrine cells were observed in mutants, compared with wild-type littermates. FIG. 4c shows the result of electron-microscopy analysis of the wild-type (upper panel) and mutant (lower panel) intestines. The density of brush-border microvilli of mutant enterocytes is reduced compared with the densely compacted, uniformly distributed microvilli of wild-type enterocytes. Scale bar: 100 μm in (a) and (b), 2 μm in (c).

Figure 5:
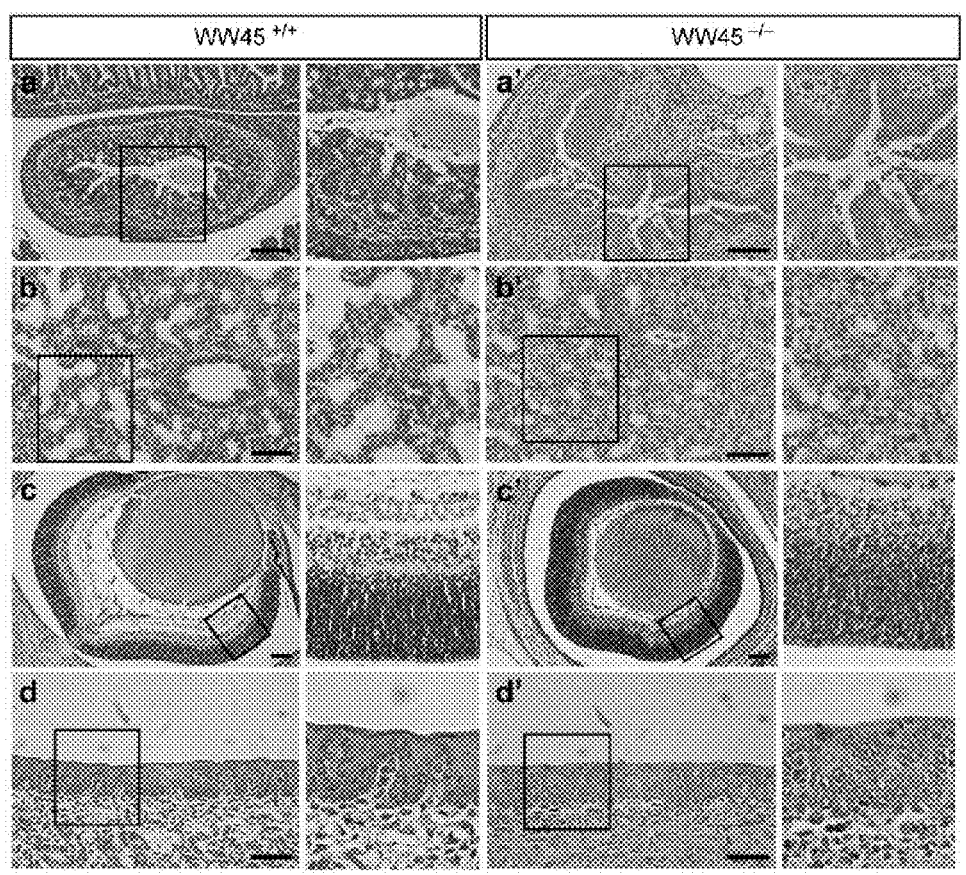
FIG. 5 shows the result of histological analysis of hematoxylin & eosin (H&E)-stained sections of wild-type (a-d) or mutant (a'-d') epithelial tissues (Scale bar: 100 μm).

FIG. 5 shows hyperplasia in WW45$^{-/-}$ epithelial tissues at E17.5. FIG. 5 shows the result of histological analysis of hematoxylin & eosin (H&E)-stained sections of wild-type (a-d) or mutant (a'-d') epithelial tissues, wherein (a, a') indicates large intestine, (b, b') lung, (c, c') retina, and (d, d') tongue. Right panels are enlarged images of each black boxed part. The dense and disorganized epithelia were observed in mutant embryos. Scale bar: 100 μm.

Figure 6:
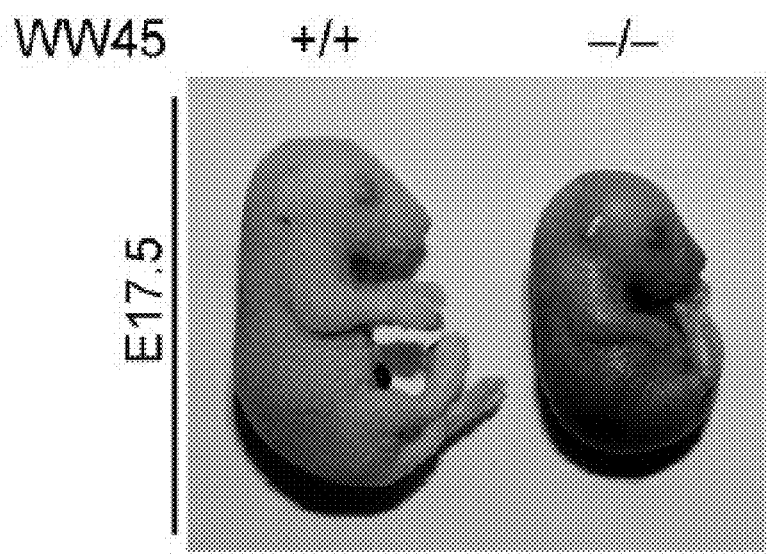
FIG. 6 shows dysmaturation of skin barrier function in mutant embryo at E17.5 measured by skin barrier function assay by X-gal staining.

There were increased numbers of keratin-10-expressing cells in the suprabasal layers of the WW45$^{-/-}$ epidermis compared with wild-type embryos (FIG. 4b-b'). Expression levels of loricrin and filaggrin, which are markers of late keratinocyte differentiation, were significantly downregulated in mutant epidermis, indicating defects in late differentiation (FIG. 4b-c'-d'). The absence of terminally differentiated layers was also confirmed by assaying skin-barrier development with X-gal staining (Hardman et al., 1998). Dye exclusion in control embryos was established at E17.5, whereas WW45$^{-/-}$ embryos turned an intense blue color when immersed in solution (FIG. 6). FIG. 6 shows dysmaturation of skin barrier function in mutant embryo at E17.5. Skin barrier function was assayed by X-gal staining. Blue-dye incorporation represents disruption to formation of the epidermal barrier in mutant embryos compared with their wild-type littermates.

Electron-microscopy analysis clearly showed that the epidermis of WW45-null embryos was thicker than the wild-type epidermis. Moreover, the granular and cornified layers present dysmaturation in the mutant epidermis, with nucleated cells reaching the epidermal surface (FIG. 3c). FIG. 3c shows the result of electron-microscopy analysis of the wild-type (upper panel) and mutant (lower panel) epidermis. The loss of columnar morphology in basal cells and the disorganized suprabasal cells were observed as well as the loss of flattened granular and cornified layers in the mutant skin.

These data indicate that the suprabasal mutant keratinocytes fail to stop proliferating and terminally differentiate.

Intestinal development in mutant embryos was also examined. Wild-type intestinal epithelium consists of a monolayer of polarized epithelial cells organized into crypts. By contrast, the WW45$^{-/-}$ mutant epithelium was multilayered and displayed hypercellularity with pseudostratified and enlarged nuclei, perturbed differentiation with loss of goblet cells, and increased numbers of mitotic cells (FIG. 4a-a' and FIG. 5-a, a'). Furthermore, Ki67 staining revealed extensive proliferation throughout the villus epithelium in the small intestine, whereas proliferative cells were restricted to the crypt bases in the control epithelium (FIG. 3a-b-b').

Figure 7A:
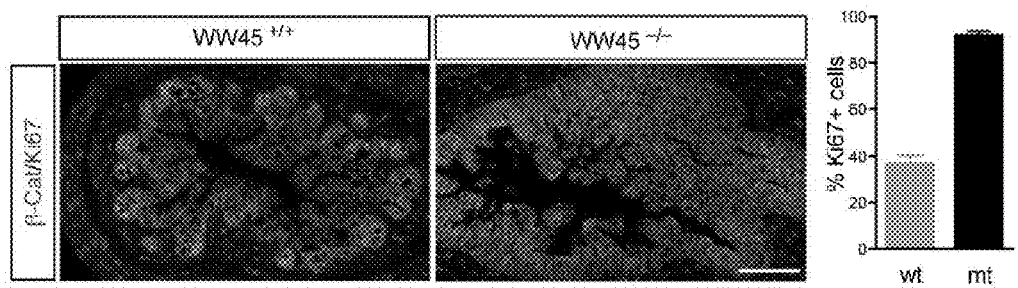
FIGS. 7a and 7b show hyperproliferation in WW45−/− epithelial tissues at E17.5, wherein 7a shows the result of evaluation of cellular proliferation in wild-type or mutant colonic epithelium by co-immunohistochemistry analysis with anti-Ki67 and anti-β-catenin (Scale bar: 100 μm), and 7b shows the result of quantitative analysis of the percentage of BrdU-positive cells per 1.0-mm$^2$ area of epithelium 2 hours after BrdU injection (Data represent triplicate independent experiments ±SD).
Figure 7B:
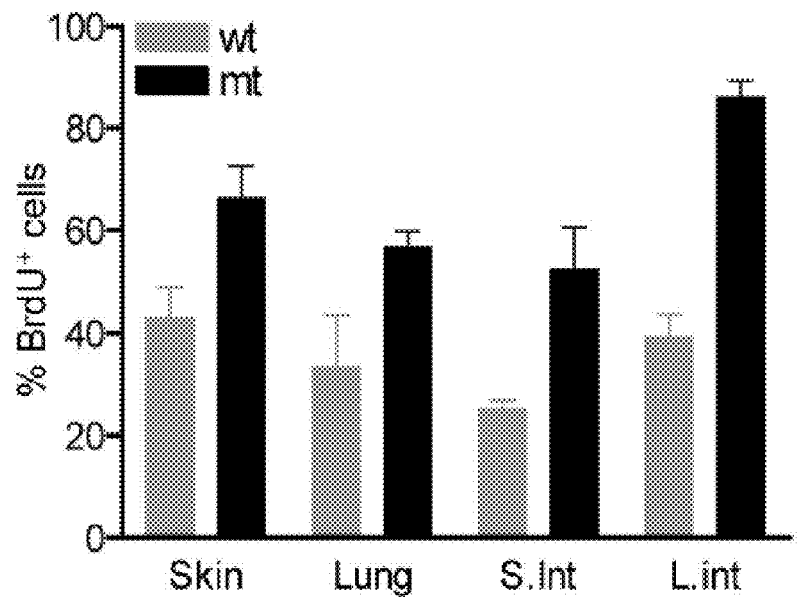

Indeed, all epithelial cells in the mutant colons were Ki67-positive, indicating dysplasia (FIG. 7a). FIG. 7 shows hyperproliferation in WW45$^{-/-}$ epithelial tissues at E17.5, wherein FIG. 7a shows the result of evaluation of cellular proliferation in wild-type or mutant colonic epithelium by co-immunohistochemistry analysis with anti-Ki67 and anti-β-catenin. The numbers of Ki67-positive cells, including those located in multiple cell layers, in the mutant epithelium were increased compared with the control epithelium; in the control epithelium, Ki67-positive cells were present mainly in the restricted proliferation zone. Scale bar: 100 μm. In agreement with these results, bromodeoxyuridine (BrdU) pulse experiments further confirmed significantly increased numbers of dividing cells in mutant epithelia of many organs (FIG. 7b). FIG. 7b shows the result of quantitative analysis of the percentage of BrdU-positive cells per 1.0-mm$^2$ area of epithelium 2 hours after BrdU injection. Data represent triplicate independent experiments ±SD.

Then, the differentiation of the various intestinal epithelial cell lineages was examined. During differentiation of enterocytes, the main epithelial cell type, the FABP protein was detected at normal levels in the villi of wild-type embryos but at markedly reduced levels in the mutant embryos (FIG. 4b-a, a'). Similarly, chromogranin labeling, which detects differentiation along the entero-endocrine lineage, was rarely detected in mutant embryos (FIG. 4b-b, b'). Staining with Alcian blue, a marker for goblet cells, revealed a complete absence of muco-secreting goblet cells in all mutant intestinal tracts (FIG. 4b-c, c'). Ultrastructural analysis also revealed poorly developed microvillus brush borders on the apical surfaces of the villous enterocytes, indicating defective enterocyte differentiation in mutant epithelium of the small intestine (FIG. 4c). Interestingly, these mutant cells had enlarged nuclei located close to the apical region, indicating a loss of apical-basal polarity.

In addition to immature differentiation of the mutant skin and intestine, immature differentiation was also detected in the lungs of mutant embryos (Lee and Lim, personal observation). Taken together, these results indicate that WW45 deficiency induces hyperplasia and immature differentiation in epithelial tissues.

Experimental Example 3

Figure 8A:
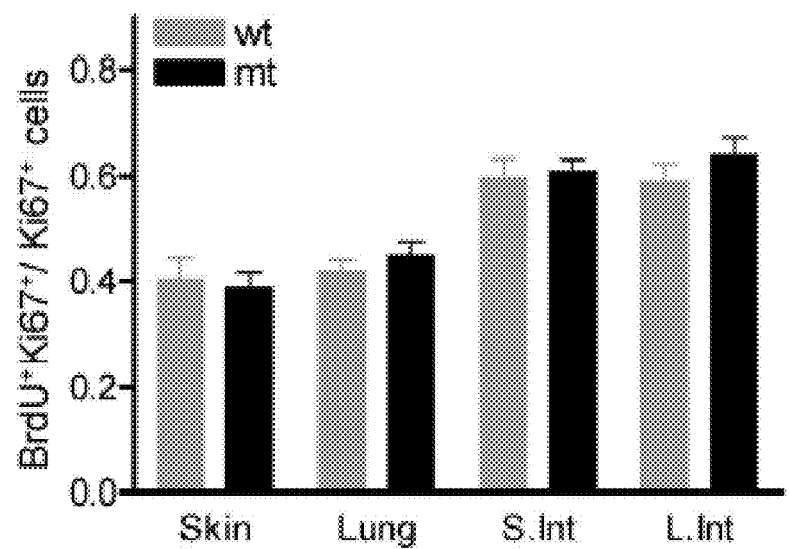
FIGS. 8a to 8d show that increased numbers of cycling cells in the developing WW45−/− epithelium is resulted from inefficient growth arrest, wherein 8a is a graph showing the proportion of progenitor cells (Ki67$^+$) labeled with BrdU after a 1-hour pulse, 8b shows the result of analysis of immunoreactivity for Ki67 in BrdU-positive cells 24 hours after BrdU injection, 8c shows growth curves of primary keratinocytes isolated from wild-type and mutant epidermis show similar proliferation rates, and 8d shows induction of calcium-stimulated differentiation in primary keratinocytes (data of a-d represent triplicate independent experiments (±SD)).

WW45 Regulates Cell-Cycle Exit in Epithelial Progenitor Cells During Differentiation It was tested whether excessive proliferation of mutant cells was due to increased proliferation rates or failure of cell-cycle exit for terminal differentiation (according to Example 2). First, the cell-cycle duration in epithelial progenitor cells was examined by analyzing the proportion of cycling cells (Ki67$^+$) in S-phase 1 hour after injection of BrdU (Schmahl, 1983). Although the percentage of BrdU-labeled cells was increased in mutant embryos, the BrdU$^+$ Ki67$^+$/Ki67$^+$ labeling index was approximately the same in wild-type and mutant embryos, indicating similar proliferation rates in wild-type and mutant embryos (FIG. 8a). FIG. 8 shows increased numbers of cycling cells in the developing WW45$^{-/-}$ epithelium resulted from inefficient growth arrest, wherein FIG. 8a is a graph showing the proportion of progenitor cells (Ki67$^+$) labeled with BrdU after a 1-hour pulse. There is no difference in cell-cycle length between wild-type and mutant embryos.

Figure 8B:
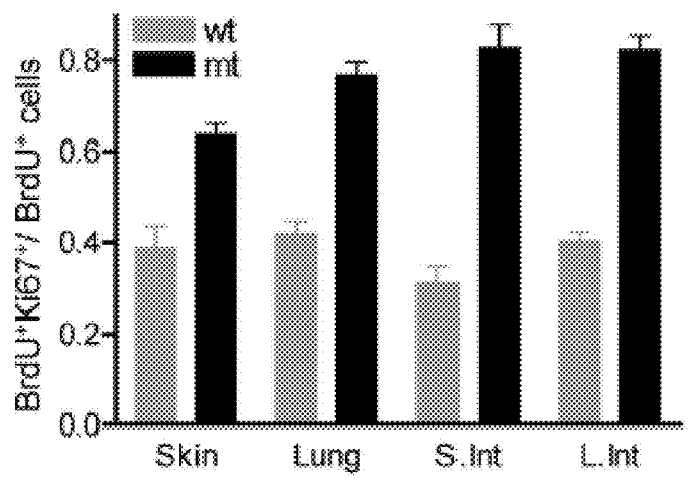

Second, the frequency of cell-cycle re-entry was determined by assessing the proportion of dividing cells (BrdU$^+$) 24 hours after the BrdU injection (Chenn and Walsh, 2002). During the time interval between BrdU application and analysis, cells can leave (Ki67$^-$) or re-enter the cell cycle (Ki67$^+$). The mean ratio of BrdU$^+$Ki67$^+$/BrdU$^+$ cells was significantly increased by 49% in the mutant small intestine and by 58% in the mutant colon compared with wild-type controls (FIG. 8b). FIG. 8b shows the result of analysis of immunoreactivity for Ki67 in BrdU-positive cells 24 hours after BrdU injection. The fraction of cells re-entering the cell cycle (BrdU$^+$Ki67$^+$) is significantly increased in mutant embryos.

The above results indicate that WW45 promotes to exit from the cell cycle in epithelial progenitors during embryonic development.

Experimental Example 4

Figure 8C:
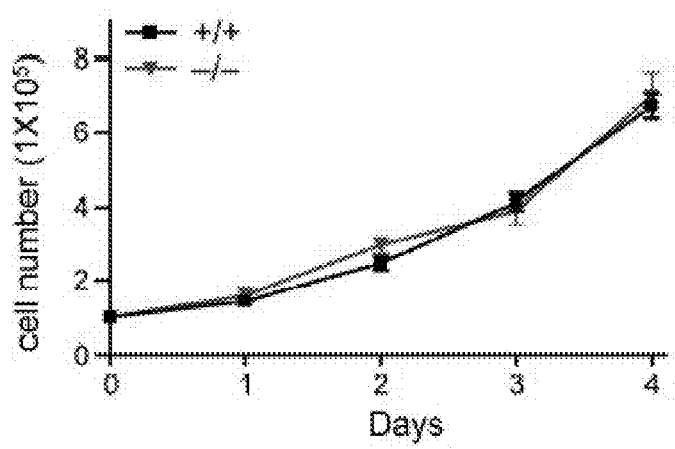

Failure of Cell-Cycle Exit of WW45$^{-/-}$ Keratinocytes During In-Vitro Differentiation To further analyze the rates of proliferation and differentiation of epithelial cells, primary keratinocytes from the skin of embryos were isolated. Consistent with in-vivo data (FIG. 8a), WW45$^{-/-}$ keratinocytes had normal cell-cycle distribution and the rate of proliferation was not significantly increased compared with control cells (FIG. 8c). FIG. 8c shows growth curves of primary keratinocytes isolated from wild-type and mutant epidermis, which shows similar proliferation rates.

In addition, the results suggest that WW45 is unlikely to regulate the rate of proliferation. The ability of WW45 to regulate proliferation arrest and differentiation of developing epidermal cells was examined by adding calcium, transforming growth factor-β (TGF-β) or lithium chloride (LiCl), which has been shown to induce proliferation exit, and possibly terminal differentiation, of keratinocytes (Hennings et al., 1980; Shipley et al., 1986; Olmeda et al., 2003). With Ca$^{2+}$, TGF-β or LiCl treatment (see Example 8), the wild-type keratinocytes showed efficient growth arrest and the numbers of BrdU-labeled cells were reduced. By contrast, mutant cells continued to proliferate and were BrdU-positive 24 hours after Ca$^{2+}$, TGF-β or LiCl treatment (FIGS. 8d and 9).

Figure 8D:
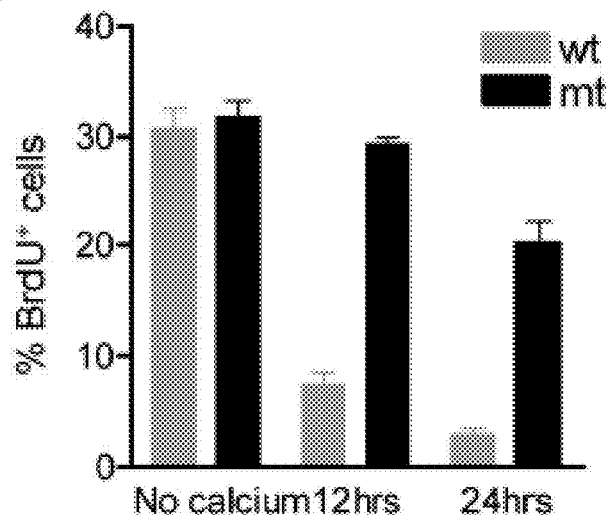
Figure 9A:
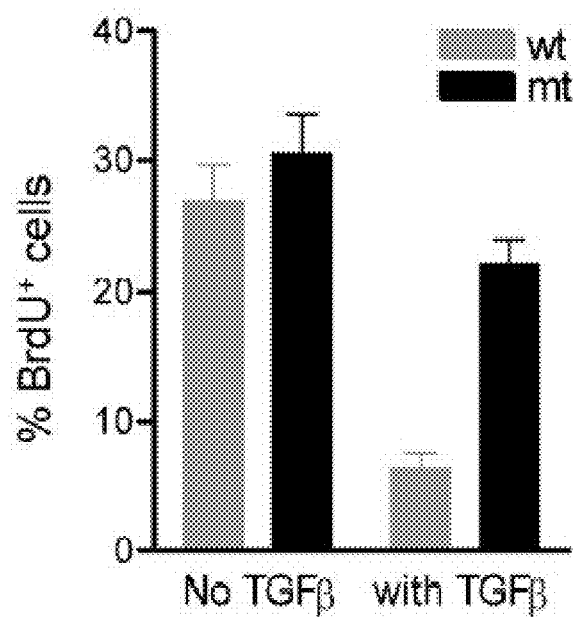
FIGS. 9a and 9b show defective cell-cycle exit in WW45−/− keratinocytes, wherein 9a and 9b show BrdU-labeling index of keratinocytes cultured with or without transforming growth factor (TGF)-β (a) or LiCl (b), respectively.
Figure 9B:
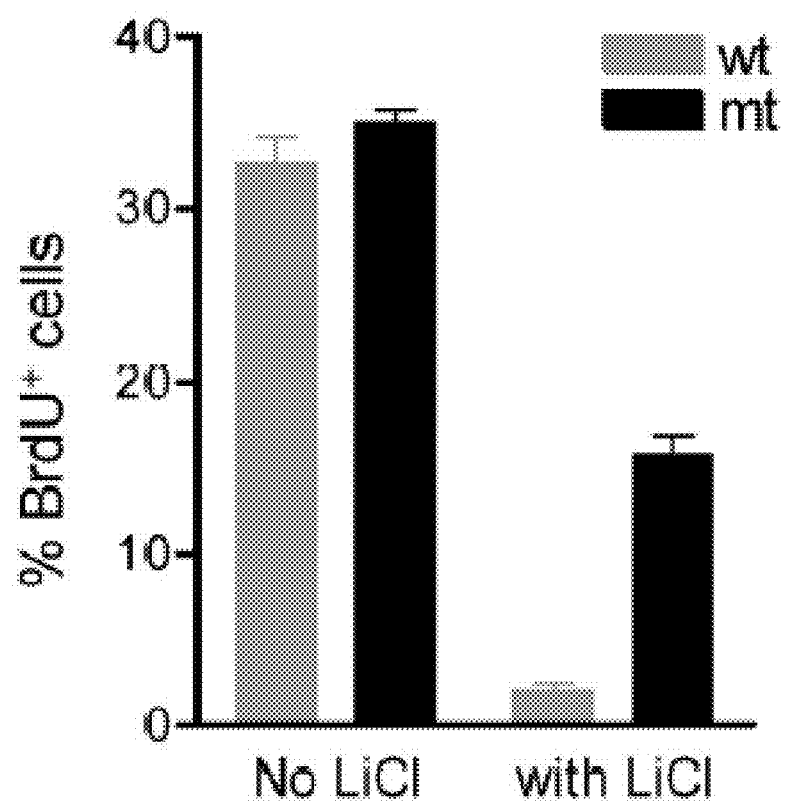

FIG. 8d is a graph showing induction of calcium-stimulated differentiation in primary keratinocytes. Level of BrdU incorporation in keratinocytes cultured in the absence or presence of Ca$^{2+}$ for the times was indicated. WW45-deficient embryos show inefficient growth arrest in the mutant keratinocytes under differentiation conditions. FIG. 9 shows defective cell-cycle exit in WW45−/− keratinocytes, wherein 9a and 9b show BrdU-labeling index of keratinocytes cultured with or without transforming growth factor (TGF)-β (a) or LiCl (b), respectively. The failure to stop cycling in WW45-deficient keratinocytes in response to TGF-β or LiCl treatment was observed.

Figure 10A:
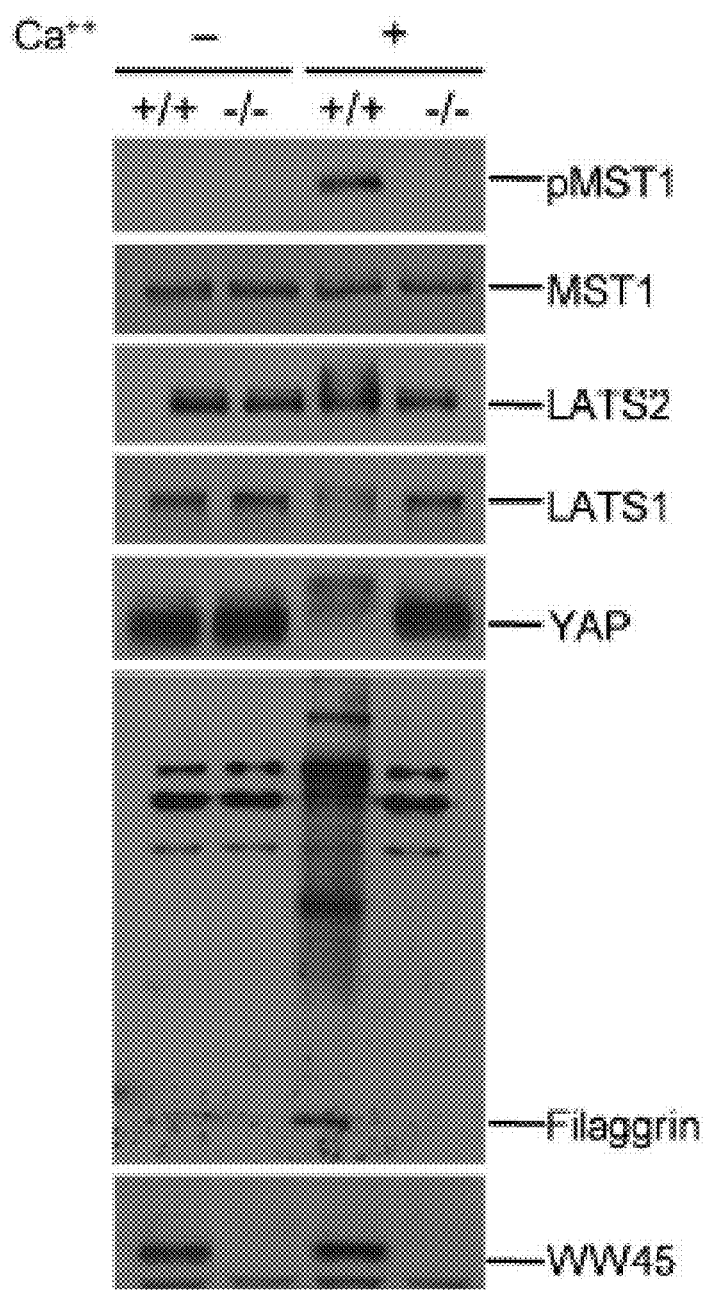
FIGS. 10a to 10c show activation of MST1 signaling pathway during differentiation, wherein 10a shows protein status of components of the MST1 pathway under differentiation conditions, 10b shows the analysis results for wild-type and mutant primary keratinocytes cultured with or without Ca2+ for 24 hours by immunoprecipitation with antibodies against MST1 and by Western-blot assays, and 10c shows phosphorylation of YAP by activated LATS2 through MST1/WW45.

WW45-deficient embryos display failure of cell-cycle exit of mutant keratinocytes under differentiation conditions. Consistent with these results, the expression of filaggrin was evident in wild-type but not mutant keratinocytes after induction of differentiation (FIG. 10a). FIG. 10 shows activation of MST1 signaling pathway during differentiation, 10a shows protein status of components of the MST1 pathway under differentiation conditions. Primary keratinocytes were incubated with or without Ca$^{2+}$ for 24 hours and analyzed by Western-blot analysis with the indicated antibodies. The activation of MST1, as shown by pMST1 blotting and the mobility shift of YAP and LATS1/2 was observed in the control keratinocytes, but not in mutant keratinocytes, under differentiation conditions. Keratinocyte differentiation was confirmed by Western-blot analysis of filaggrin expression.

These data indicate that increased proliferation in WW45$^{-/-}$ epithelial tissues results from impaired growth arrest of progenitor cells during differentiation rather than from an increased rate of proliferation.

Experimental Examine 5

Activation of the MST Signaling Pathway During Keratinocyte Differentiation In Vitro To further characterize the molecular mechanisms by which WW45 regulates cell-cycle exit during differentiation, the phosphorylation and localization of MST, LATS and YAP in keratinocytes during differentiation were investigated. Interestingly, autophosphorylation of MST1 was induced upon differentiation, as shown by phospho-MST1 immunoblotting, indicating MST1 activation (FIG. 10a). By contrast, this autophosphorylation of MST1 was not detected in the WW45$^{-/-}$ keratinocytes. Therefore, WW45 is required for MST1 activation after induction of differentiation with calcium treatment. In addition, the mobility patterns of LATS1/2 and YAP differ after induction of differentiation with calcium treatment (FIG. 10a). Phosphorylation of LATS1/2 and YAP was detected in differentiated wild-type keratinocytes, but not differentiated mutant keratinocytes. Thus, phosphorylation of YAP seems to be dependent on the MST1 signaling pathway, in particular on LATS1/2, during epithelial differentiation in mammals.

Figures 11, 12A:
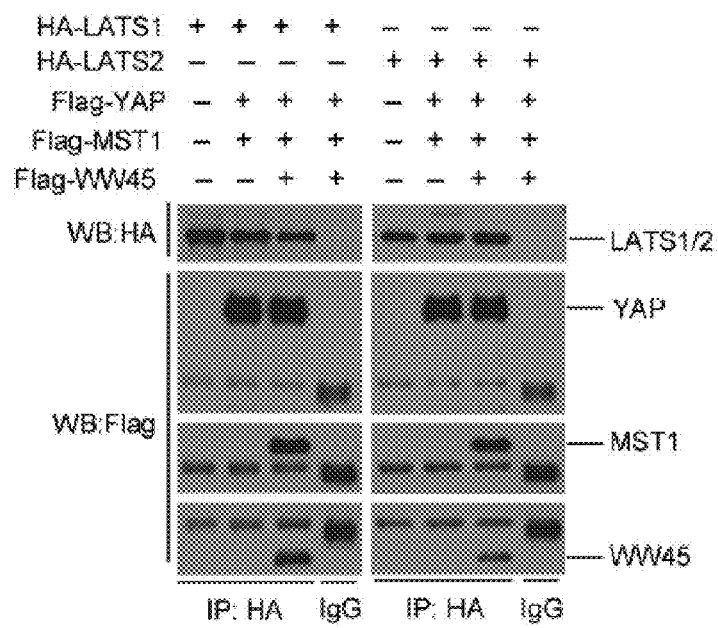
FIG. 11 shows the result of western-blot analysis with the indicated antibodies wherein the analysis was conducted for precipitates obtained from immunoprecipitation with anti-hemagglutinin (HA) in WW45−/− primary keratinocytes.
FIG. 12a shows partial alignment of the conserved regions of YAP with the *Drosophila* Yki protein.
Figure 12B:
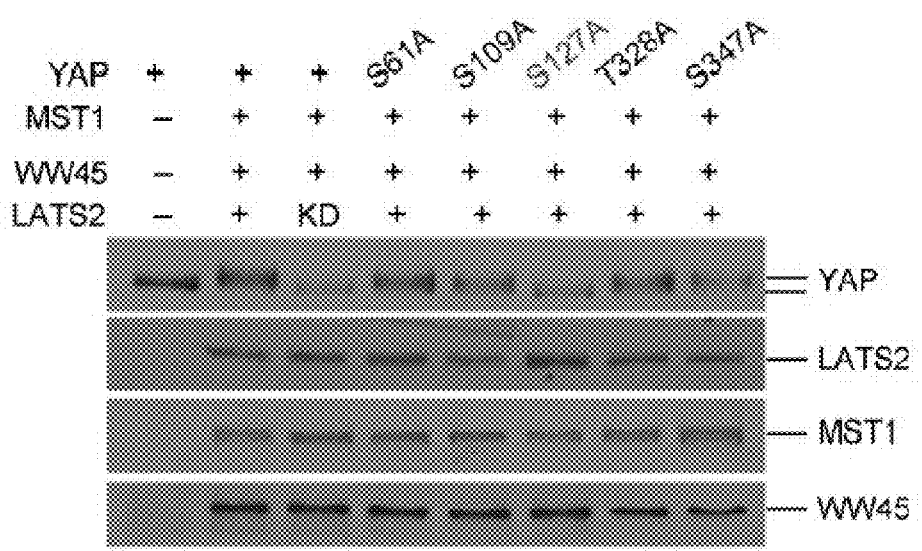
FIG. 12b shows the result of identification of the phosphorylation site of YAP.
Figure 12C:
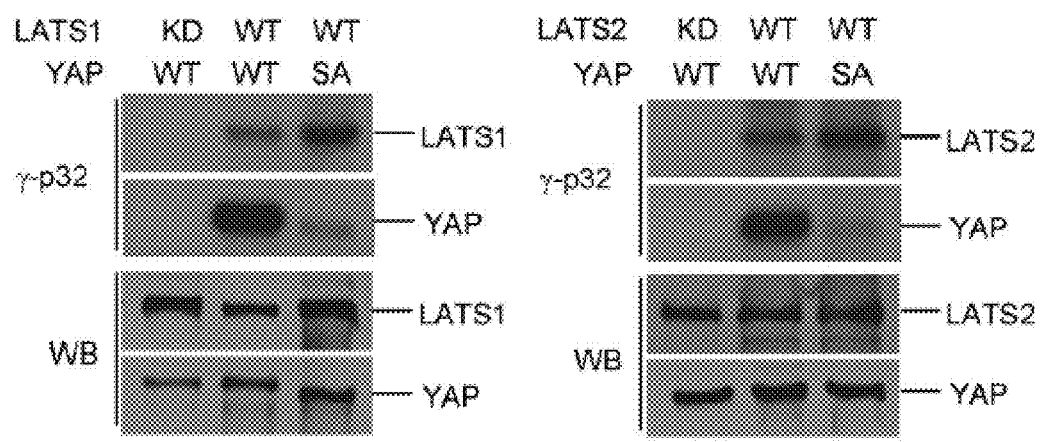
FIG. 12c shows the result from In-vitro kinase assays using immunoprecipitated HA-tagged LATS1/2 WT or KD and purified His-YAP-WT or His-YAP-SA, where the signals are shown by autoradiography analysis (top two panels); and the input kinase and substrate for Western-blot analysis using anti-LATS1/2 and anti-YAP (bottom two gels)
Figure 12D:
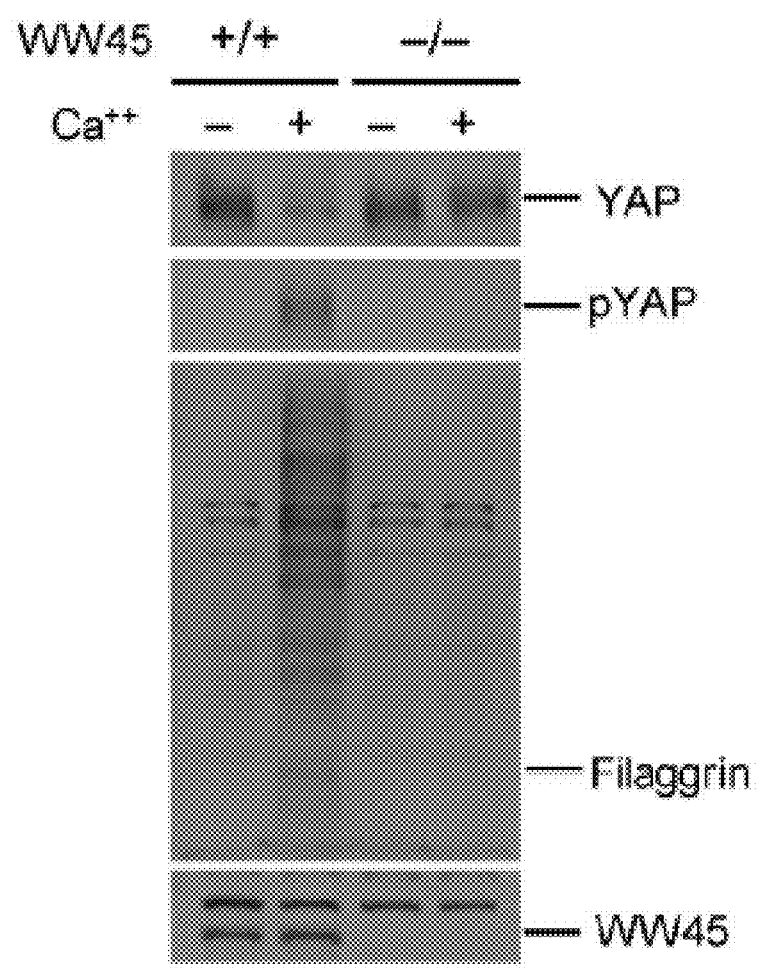
FIG. 12d shows the result of western-blot analysis with anti-YAP or an antibody specific for the serine-127-phosphorylated YAP (p-YAP) in wild-type and mutant primary keratinocytes cultured with or without Ca2+ for 24 hours.

It was also investigated whether the formation of components of the MST1 signaling pathway might be associated with and affect differentiation of keratinocytes. First, WW45$^{-/-}$ keratinocytes were transfected with LATS1/2, MST1 and YAP with or without WW45, and then induced differentiation prior to immunoprecipitation. In WW45-deficient keratinocytes, LATS1 and LATS2 co-precipitated with YAP, but not with MST1. By contrast, these proteins form a stable complex in the presence of WW45 (FIG. 11). FIG. 11 shows requirement of WW45 for interaction between MST1/2 and LATS1/2 in primary keratinocytes. Physical associations between MST1, LATS1/2, WW45 and YAP under differentiation conditions were observed. WW45$^{-/-}$ primary keratinocytes were co-transfected with the plasmids indicated at the top of each panel. After 24 hours of transfection, cells were maintained in Ca$^{2+}$-containing medium for a further 24 hours before harvesting for immunoprecipitation with anti-hemagglutinin (HA). The resulting precipitates were subjected to Western-blot analysis with the indicated antibodies. Note that complex formation was only detected in the presence of WW45.

Figure 10B:
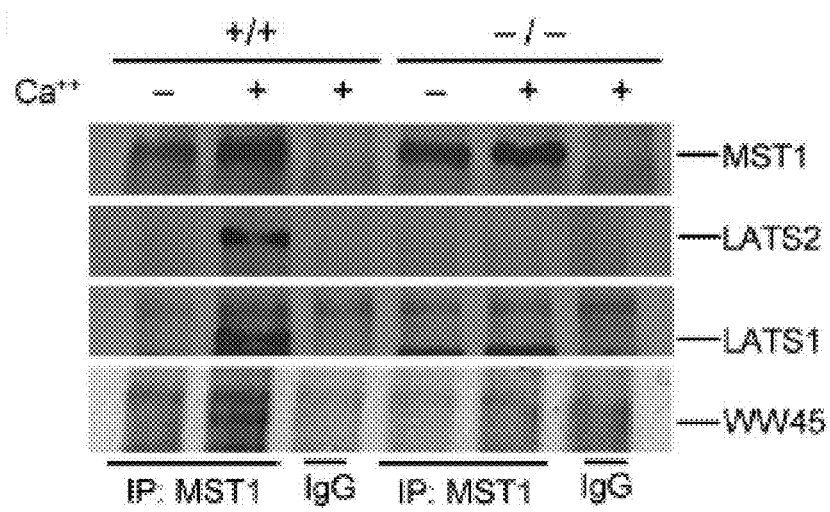
Figure 10C:
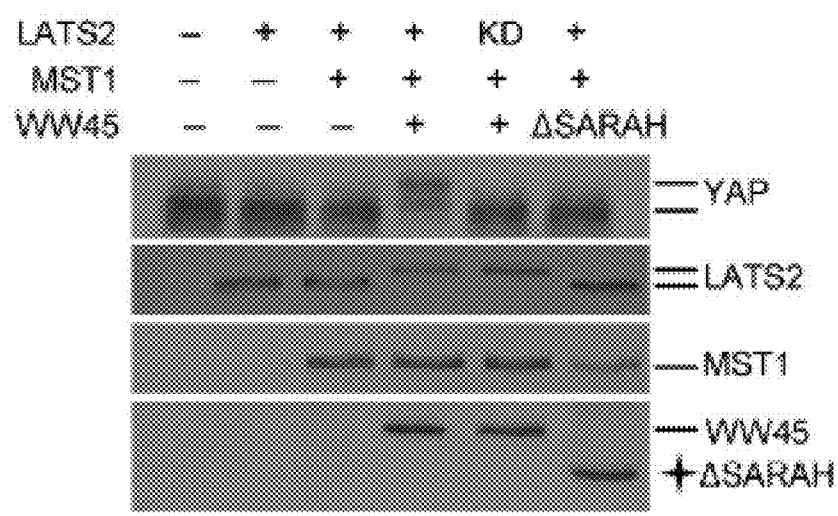

Moreover, endogenous MST1 and LATS1/2 formed a complex in keratinocytes under differentiated conditions and in the presence of WW45 (FIG. 10b). FIG. 10b shows the analysis results for wild-type and mutant primary keratinocytes cultured with or without Ca$^{2+}$ for 24 hours by immunoprecipitation with antibodies against MST1 and by Western-blot assays. Complex formation is only detected with Ca$^{2+}$ treatment in the control samples. In addition, YAP was fully phosphorylated in keratinocytes complemented with wild-type WW45 and expressing LATS2 wild-type (WT), but not in cells with wild-type WW45 and expressing LATS2 kinase dead (KD) and MST1 or in cells complemented with WW45 lacking the SARAH-domain, which is responsible for interaction with MST1 (FIG. 10c). FIG. 10c shows phosphorylation of YAP by activated LATS2 through MST1/WW45. WW45$^{-/-}$ primary keratinocytes were co-transfected with the indicated plasmids and probed with the indicated antibodies. The mobility shift of YAP and LATS2 in the presence of MST1 and intact WW45 was observed.

These results indicate that, in mammals, WW45 is required for MST1 activation and promotes LATS1/2 phosphorylation by recruiting MST1 into the complex, and that activated LATS1/2 then phosphorylates YAP. Surprisingly, activation of the MST1 signaling pathway in mammals seems to be specific for differentiation signals, at least for keratinocyte differentiation.

Then, the YAP residue that is phosphorylated by LATS1/2 was identified (FIG. 12). Key conserved residues between human YAP and *Drosophila* Yki were mutated to alanine (S61A, S109A, S127A, S328A, and S347A). Among these, only the S127A mutant was not phosphorylated by activated LATS2 in cells (FIG. 12b). Indeed, in-vitro kinase assays further showed markedly reduced levels of phosphorylation of YAP S127A mutant by LATS1/2, indicating that serine 127 is a major phosphorylation site (FIG. 12c). This result is consistent with the recent finding that serine 127 of YAP is the primary Hippo-responsive phosphorylation site (Dong et al., 2007). Finally, it was confirmed that this is a phosphorylation site of endogenous YAP with a phospho-serine 127 antibody during keratinocyte differentiation (FIG. 12d).

FIG. 12 shows that phosphorylation of YAP serine 127 by LATS1/2 in the MST1 pathway is induced by differentiation signals in primary keratinocytes. FIG. 12a shows partial alignment of the conserved regions of YAP with the *Drosophila* Yki protein. The consensus motif of the site phosphorylated by LATS1/2 is underlined. Asterisk indicates the YAP serine 127 residue, which is the phosphorylation site for LATS1/2. FIG. 12b shows the result of identification of the phosphorylation site of YAP. WW45-deficient primary keratinocytes were co-transfected with the indicated plasmids and probed with the indicated antibodies. FIG. 12c shows the result of In-vitro kinase assays that are performed using immunoprecipitated HA-tagged LATS1/2 WT or KD and purified His-YAP-WT or His-YAP-SA, wherein the signals are shown by autoradiography analysis (top two panels). The input kinase and substrate for Western-blot analysis using anti-LATS1/2 and anti-YAP are also shown (bottom two gels). FIG. 12d shows the result of Western-blot analysis with anti-YAP or an antibody specific for the serine-127-phosphorylated YAP (p-YAP) in wild-type and mutant primary keratinocytes cultured with or without Ca$^{2+}$ for 24 hours. Differentiation of keratinocytes and the presence of WW45 were assessed by Western-blot analysis using anti-filaggrin and anti-WW45.

Experimental Example 6

Dynamic Cellular Localizations of MST1 and YAP During Epithelial Differentiation YAP associates with the Src family kinase at the plasma membrane, with 14-3-3 family proteins in the cytoplasm and with transcription factors in the nucleus, suggesting a dynamic localization of YAP in cells (Sudol, 1994; Yagi et al., 1999; Vassilev et al., 2001; Mattallansa et al., 2007). However, the localization of other components of MST1 pathway has not been determined. Thus, the subcellular localization of MST1 pathway components during epithelial cell differentiation by nuclear-cytoplasmic fractionation experiments was examined. MST1 was mainly detected in the cytoplasmic fraction under undifferentiated conditions, but a significant amount was detected in the nuclear fraction after differentiation induction in wild-type cells, suggesting that differentiation triggered MST1 translocation to the nucleus.

Figure 13A:
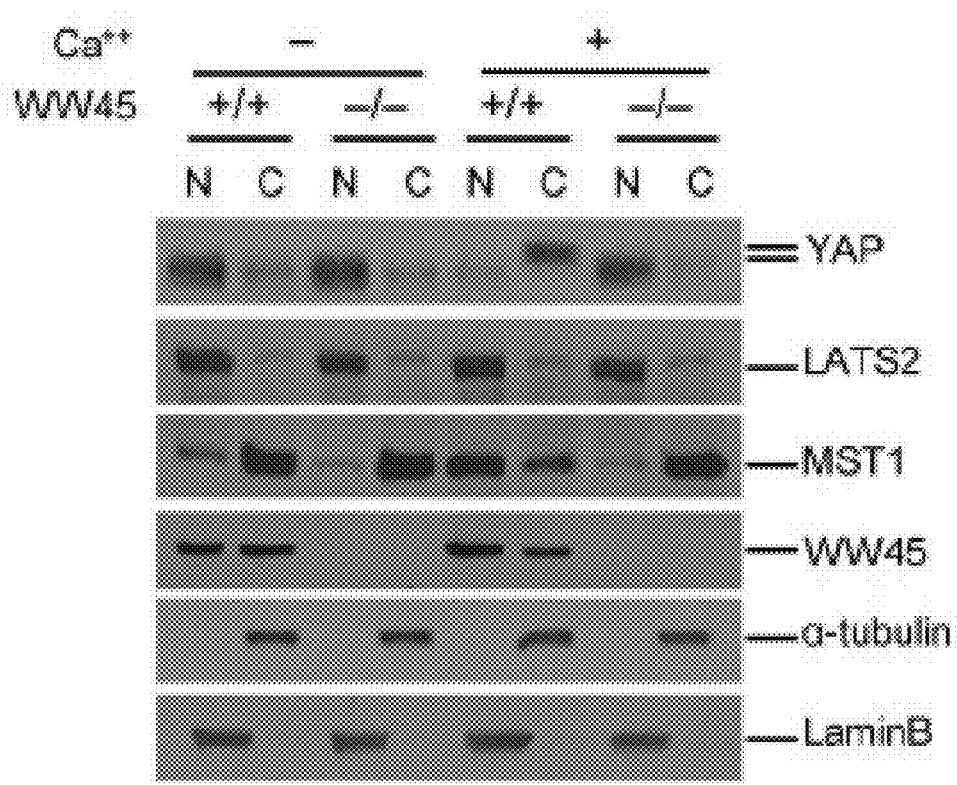
FIGS. 13a to 13d show dynamic localization of MST1/YAP during differentiation, wherein 13a to 13c show subcellular localizations of MST1 and YAP in response to differentiation stimuli, and 13d shows the result of immuno peroxidase staining for MST1, YAP and p-YAP in wild-type (a-f) and mutant (a'-f') epithelium at E17.5 (Scale bar: 10 μm in (c) and 100 μm in (d)).

However, this nuclear localization of MST1 was severely compromised in mutant cells (FIG. 13a). In addition to this change in MST1 localization, it was also found that YAP was found mainly in the nucleus under undifferentiated conditions, but it was phosphorylated and mainly detected in the cytoplasm of differentiated wild-type cells. However, cytoplasmic localization and phosphorylation of YAP were compromised in mutant cells under differentiated conditions (FIG. 13a). These results indicate that induction of keratinocyte differentiation triggers translocation of MST1 into the nucleus and then activates LATS1/2, which in turn phosphorylates YAP, and that WW45 is necessary for this event.

FIG. 13 shows dynamic localization of MST1/YAP during differentiation, 13a to 13c show subcellular localizations of MST1 and YAP in response to differentiation stimuli. In FIG. 13a, fractionation experiments were conducted with primary keratinocytes from wild-type or mutant embryos with or without $Ca^{2+}$ for 24 hours. Fractionated lysates were subjected to Western-blot analysis with the indicated antibodies. N, nuclear; C, cytoplasmic.

The ability of MST1/WW45/LATS2 to modulate the localization of YAP was further examined by ectopically overexpressing these proteins in WW45-null keratinocytes. Consistent with previous results, YAP was phosphorylated by LATS2 and this phosphorylated form was found in the cytoplasm, probably owing to nuclear translocation of MST1 by WW45 (FIG. 13b).

Figure 13B:
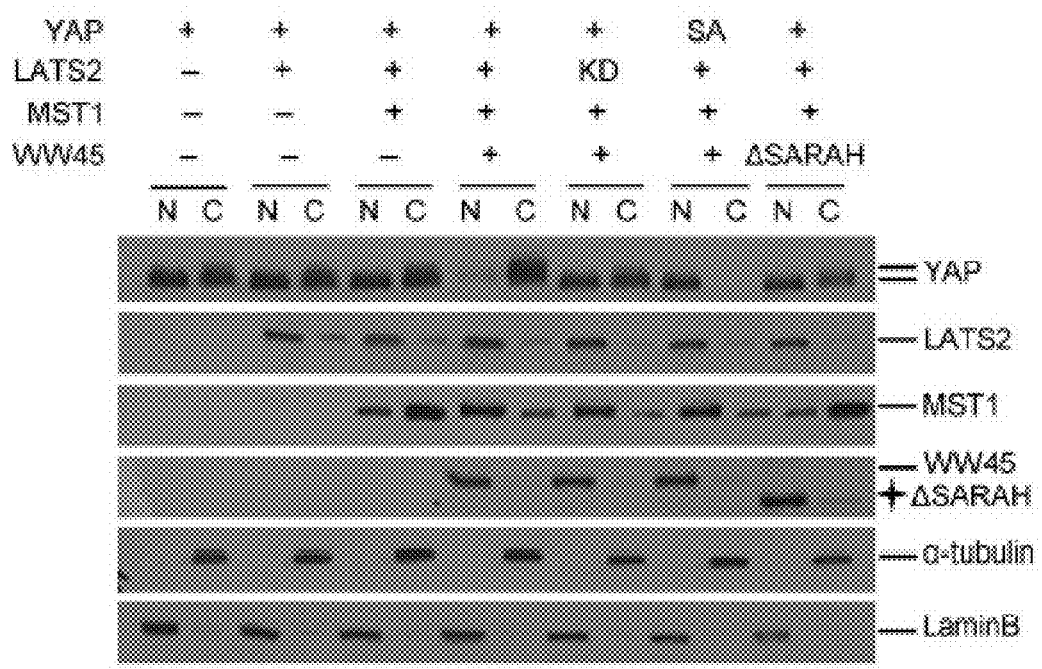

FIG. 13b shows the result obtained by co-transfecting WW45-deficient keratinocytes with the indicated plasmids. After 24 hours of transfection, cells were maintained in $Ca^{2+}$ medium for a further 24 hours before harvesting for fractionation experiments. Western-blot analysis was performed with the indicated antibodies. It is revealed that the major cytoplasm translocation of YAP and nuclear translocation of MST1 were only detected in the presence of intact WW45.

By contrast, these dynamic localizations of MST1 and YAP were not seen in cells expressing WW45 lacking the SARAH domain, which indicates that the WW45 SARAH domain is required for this process. Moreover, the YAP S127A mutant was mainly localized to the nucleus regardless of MST1 signaling activation, indicating that phosphorylation of serine 127 of YAP by LATS2 in the nucleus promotes translocation of YAP into the cytoplasm. These results are consistent with the presence of a MST1/WW45/LATS/YAP complex in differentiated keratinocytes (FIG. 10b).

Figure 13C:
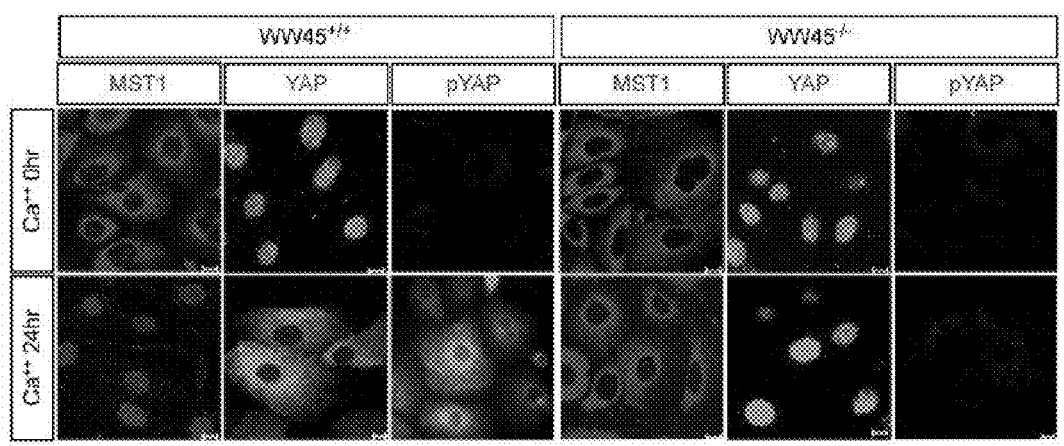
Figure 13D:
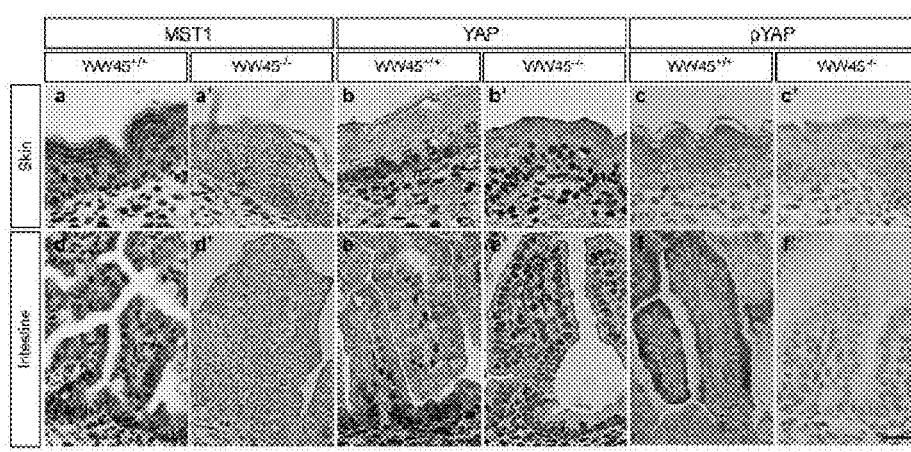

The distinct localization of MST1 and YAP was also examined by performing an immunostaining assay in differentiated keratinocytes as well as embryo tissue sections (FIG. 13c and 13d). FIG. 13c shows the result obtained by culturing primary keratinocytes from wild-type or mutant embryos with or without $Ca^{2+}$ for 24 hours, and then, being subjected to immunostaining with anti-MST1, anti-YAP and anti-p-YAP. The phospho-dependent translocation of YAP and MST1 was observed in $Ca^{2+}$-induced differentiated control cells, but not in mutant cells. FIG. 13d shows the result of immunoperoxidase staining for MST1, YAP and p-YAP in wild-type (a-f) and mutant (a'-f') epithelium at E17.5. The intense nuclear detection of YAP and cytoplasmic detection of MST1 in most mutant epithelia cells were observed, which is in contrast to the dynamic distributions according to differentiation stage in control epithelial cells. Serine 127 phosphospecific immunoreactivity was cytoplasm-specific in the differentiating zones in the control, whereas the signal was absent from the mutant cells. Counterstaining was performed with hematoxylin. (a-c, a'-c') Skin. (d-f, d'-f') Small intestine. Scale bar: 10 μm in (C) and 100 μm in (D).

Figure 14A:
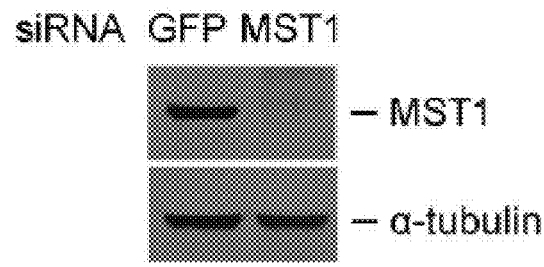
FIG. 14a shows the result of western-blot analysis performed for lysates of HeLa cells stably transfected with a vector encoding MST1 siRNA or GFP siRNA as a control.
Figure 14B:
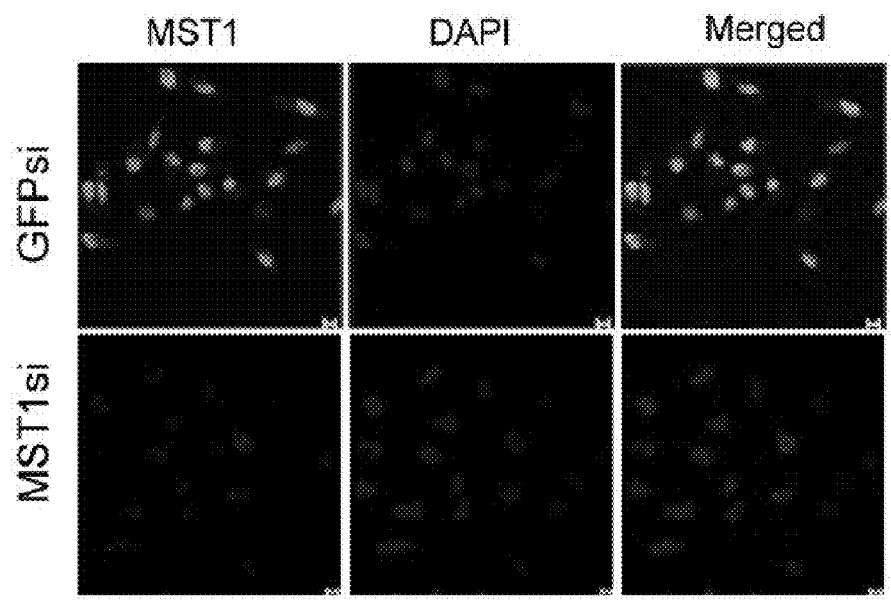
FIG. 14b shows the result from staining Control- and MST1-siRNA-expressing HeLa cells with DAPI and MST1 antibody.

The specificity of MST1 antibody was verified by immunostaining and immunoblot using MST1-deleted cells (FIG. 14). FIG. 14 shows the verification of the MST1 antibody, wherein FIG. 14a shows the result from Western-blot analysis that was performed with lysates of HeLa cells stably transfected with a vector encoding MST1 siRNA or GFP siRNA as a control. α-tubulin was used as a loading control. FIG. 14b shows the results obtained by staining control- and MST1-siRNA-expressing HeLa cells with DAPI and with MST1 antibody.

Figure 15:
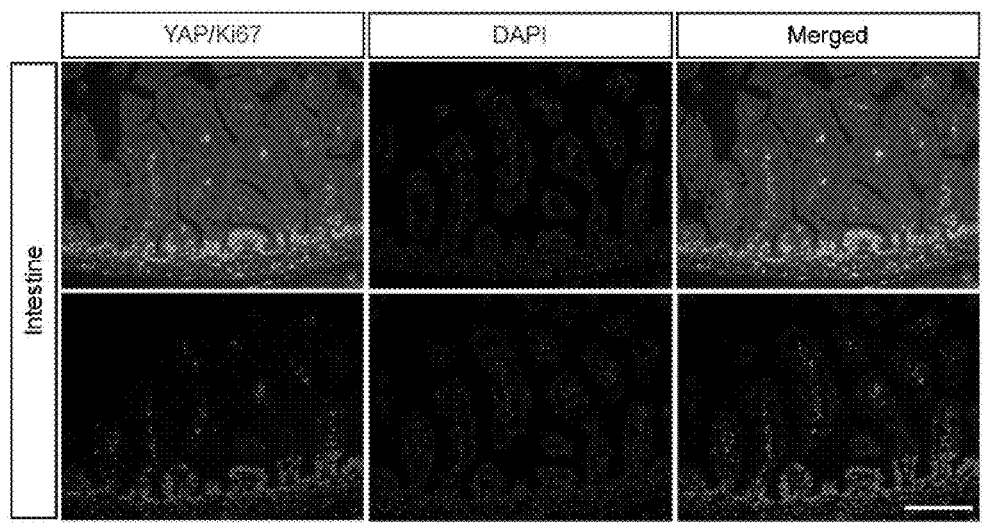
FIG. 15 shows nuclear localization of YAP in proliferative progenitor compartment of the small intestine (Scale bar: 100 μm).

Consistent with the fractionation results, staining for MST1 and YAP revealed dynamic translocation of endogenous YAP and MST1 during differentiation in the wild-type keratinocytes but such translocation was not apparent in the mutant keratinocytes during differentiation (FIG. 13c). Moreover, although phosphorylated YAP was evident and mainly found in the cytoplasm in differentiated wild-type cells, it was barely detectable in mutant cells. In wild-type tissue sections, the inventors detected nuclear-localized YAP in proliferative basal cells, which were Ki67-positive, and cytoplasm-localized YAP in differentiated cells (FIG. 13d and FIG. 15). FIG. 15 shows nuclear localization of YAP in proliferative progenitor compartment of the small intestine. The serial sections of the wild-type embryos were stained with anti-YAP and anti Ki67. The nuclear-localized YAP in the Ki67-positive cycling cells of the crypt compartment of the small intestine was detected. Scale bar: 100 μm. These results are consistent with the recent finding that YAP is expressed and localized in the nuclei of the crypt compartment of the small intestine (Camargo et al., 2007).

However, MST1 was detected in the cytoplasm of proliferating cells, but in the nucleus of differentiated cells in the wild-type skin and intestine. By contrast, many proliferating cells of mutant embryos showed cytoplasm-localized MST1 and nuclear-localized YAP (FIG. 13d). In addition to changes in MST1 and YAP localizations, the cytoplasm of the differentiated regions in control embryos stained positive for phosphor-YAP, but staining levels were significantly reduced in mutant embryos (FIG. 13d). Therefore, consistent with in-vitro epithelial differentiation results, the changes in dynamic localization of MST1 and YAP are also likely to occur as epithelial cells undergo differentiation in vivo, and WW45 is likely to be a key protein in this process.

Experimental Example 7

Failure of Proliferation Arrest and Differentiation of Normal Keratinocytes Expressing YAP S127A Based on our observations that phosphorylation and translocation of YAP into the cytoplasm are dependent on LATS1/2, which acts via MST1/WW45, it was assessed whether the phosphorylation of serine 127 of YAP is required for inducing keratinocyte growth arrest and differentiation. Thus, keratinocytes were infected with a retrovirus expressing YAP WT, YAP S127A, which is a non-phospho form, or YAP S127D, which is a phospho-mimic form. Calcium-induced differentiation signals suppressed proliferation of growing keratinocytes expressing YAP WT or YAP S127D. By contrast, YAP S127A was mainly localized to the nucleus and its overexpression in wild-type keratinocytes failed to cause proliferation arrest and differentiation (FIG. 16a to 16c).

These results indicate that the non-phosphorylated form of YAP is localized to and acts in the nucleus to allow cells to proliferate even in the presence of differentiation signals. It was also tested whether inactivation of YAP suppresses the differentiation defect in the WW45-deficient keratinocytes.

To do this, the dominant-negative form of YAP (DN), which dominantly inhibits the function of endogenous YAP protein, was generated (Zhao et al., 2007). Importantly, YAP DN was sufficient to rescue the differentiation of the mutant cells (FIGS. 16d and 16e). Taken together, these results show that inactivation and subcellular targeting to the cytoplasm of phosphorylated YAP is required for cell-cycle exit and differentiation initiation.

FIG. 16 shows the effects of phosphorylation of YAP serine 127 on epithelium differentiation. FIG. 16a shows the percentage of proliferative cells labeled with BrdU under differentiation conditions. Levels of BrdU incorporation in primary keratinocytes were determined at the indicated times after retroviral infection with the indicated genes and incubation with or without $Ca^+$. WT, wild-type; SA, S127A mutant, SD, S127D mutant. The failure of cell-cycle exit in response to $Ca^{2+}$-induced differentiation in YAP-SA-infected cells was observed.

FIG. 16b shows the failure of YAP-SA-infected cells to differentiate in response to differentiation stimuli. Lysates from 16a were subjected to Western-blot analysis with the indicated antibodies. The suppression of YAP mobility shift with the absence of processed forms of filaggrin, which is a late-terminal differentiation marker, in YAP-SA-infected cells, was observed.

FIG. 16c shows subcellular localization of YAP, YAP SA and YAP SD in response to differentiation stimuli. Fractionations from 16a were subjected to immunoblot analysis with the indicated antibodies. The lack of cytoplasmic translocation of YAP SA under the $Ca^{2+}$-induced differentiation conditions was observed.

FIG. 16d shows the percentage of BrdU-positive cells in WW45-deficient keratinocytes infected with the indicated genes under differentiation conditions. WT, wild-type; DN, dominant negative form. The suppression of cell-cycle re-entry in response to $Ca^{2+}$ treatment in WW45-deficient keratinocytes infected with YAP-DN was observed.

FIG. 16e shows the result of Western-blot analysis on lysates from 16d with the indicated antibodies. The rescue of differentiation in response to $Ca^{2+}$ treatment in WW45-deficient keratinocytes infected with YAP-DN was observed.

FIG. 16f shows a proposed model for the role of WW45 in developing epithelial tissues. Under differentiation conditions, WW45 promotes LATS1/2 phosphorylation by recruiting MST1/2 into the nuclear-localized complex, and this activated LATS1/2 then phosphorylates YAP, resulting in translocation of YAP into the cytoplasm.

This phosphorylation and subcellular targeting of YAP to the cytoplasm are required for proliferation stop and differentiation initiation in developing epithelial cells. Ultimately, during development, the MST1 pathway regulates proper epithelial tissue development by controlling the balance between proliferation and terminal differentiation.

What is claimed is:

1. A transgenic mouse whose genome comprises a heterozygous, null allele of the gene encoding WW45 protein, wherein at least the region encoding the SARAH domain of the WW45 protein is deleted, and wherein said mouse exhibits formation of tumors.

2. The transgenic mouse according to claim 1, wherein the gene encoding WW45 protein is the gene encoding mouse WW45 protein (SEQ ID NO: 8).

3. The transgenic mouse according to claim 1, wherein the SARAH domain has the amino acid sequence of SEQ ID NO: 11.

4. A method of screening a compound for anti-tumor activity, the method comprising the steps of:
preparing a transgenic mouse whose genome comprises a heterozygous, null allele of the gene encoding WW45 protein, wherein at least the region encoding the SARAH domain of the WW45 protein is deleted, and wherein said mouse exhibits formation of tumors;
treating the prepared transgenic mouse with a candidate compound;
determining a level of the tumor in the transgenic mouse treated with the candidate compound by measuring the number of tumor cells, volume of the tumor, or tumor cell viability; and
identifying the candidate compound as a compound having anti-tumor activity if the number of the tumor cells or the volume of the tumor has been decreased relative to the number of tumor cells or volume of the tumor in the transgenic mouse prior to the treatment with the candidate compound, or if apoptosis of the tumor cells has been induced after the treatment with the candidate compound.

5. The method according to claim 4, wherein the compound has anti-tumor activity against osteosarcoma or hepatoma.

* * * * *

SEQUENCE LISTING

<160> NUMBER OF SEQ ID NOS: 20

<210> SEQ ID NO 1
<211> LENGTH: 383
<212> TYPE: PRT
<213> ORGANISM: Artificial Sequence
<220> FEATURE:
<223> OTHER INFORMATION: amino acid sequence of human WW45 protein

<400> SEQUENCE: 1

```
Met Leu Ser Arg Lys Lys Thr Lys Asn Glu Val Ser Lys Pro Ala Glu
 1               5                  10                  15

Val Gln Gly Lys Tyr Val Lys Lys Glu Thr Ser Pro Leu Leu Arg Asn
             20                  25                  30

Leu Met Pro Ser Phe Ile Arg His Gly Pro Thr Ile Pro Arg Arg Thr
         35                  40                  45

Asp Ile Cys Leu Pro Asp Ser Ser Pro Asn Ala Phe Ser Thr Ser Gly
     50                  55                  60

Asp Val Val Ser Arg Asn Gln Ser Phe Leu Arg Thr Pro Ile Gln Arg
 65                  70                  75                  80

Thr Pro His Glu Ile Met Arg Arg Glu Ser Asn Arg Leu Ser Ala Pro
                 85                  90                  95

Ser Tyr Leu Ala Arg Ser Leu Ala Asp Val Pro Arg Glu Tyr Gly Ser
            100                 105                 110

Ser Gln Ser Phe Val Thr Glu Val Ser Phe Ala Val Glu Asn Gly Asp
        115                 120                 125

Ser Gly Ser Arg Tyr Tyr Tyr Ser Asp Asn Phe Phe Asp Gly Gln Arg
    130                 135                 140

Lys Arg Pro Leu Gly Asp Arg Ala His Glu Asp Tyr Arg Tyr Tyr Glu
145                 150                 155                 160

Tyr Asn His Asp Leu Phe Gln Arg Met Pro Gln Asn Gly Arg His
                165                 170                 175
```

```
Ala Ser Gly Ile Gly Arg Val Ala Ala Thr Ser Leu Gly Asn Leu Thr
            180                 185                 190

Asn His Gly Ser Glu Asp Leu Pro Leu Pro Pro Gly Trp Ser Val Asp
            195                 200                 205

Trp Thr Met Arg Gly Arg Lys Tyr Tyr Ile Asp His Asn Thr Asn Thr
210                 215                 220

Thr His Trp Ser His Pro Leu Glu Arg Glu Gly Leu Pro Pro Gly Trp
225                 230                 235                 240

Glu Arg Val Glu Ser Ser Glu Phe Gly Thr Tyr Tyr Val Asp His Thr
            245                 250                 255

Asn Lys Lys Ala Gln Tyr Arg His Pro Cys Ala Pro Ser Val Pro Arg
            260                 265                 270

Tyr Asp Gln Pro Pro Val Thr Tyr Gln Pro Gln Thr Glu Arg
            275                 280                 285

Asn Gln Ser Leu Leu Val Pro Ala Asn Pro Tyr His Thr Ala Glu Ile
            290                 295                 300

Pro Asp Trp Leu Gln Val Tyr Ala Arg Ala Pro Val Lys Tyr Asp His
305                 310                 315                 320

Ile Leu Lys Trp Glu Leu Phe Gln Leu Ala Asp Leu Asp Thr Tyr Gln
                325                 330                 335

Gly Met Leu Lys Leu Leu Phe Met Lys Glu Leu Glu Gln Ile Val Lys
            340                 345                 350

Met Tyr Glu Ala Tyr Arg Gln Ala Leu Leu Thr Glu Leu Glu Asn Arg
            355                 360                 365

Lys Gln Arg Gln Gln Trp Tyr Ala Gln Gln His Gly Lys Asn Phe
            370                 375                 380

<210> SEQ ID NO 2
<211> LENGTH: 386
<212> TYPE: PRT
<213> ORGANISM: Artificial Sequence
<220> FEATURE:
<223> OTHER INFORMATION: amino acid sequence of mouse WW45 protein

<400> SEQUENCE: 2

Met Leu Ser Arg Lys Lys Thr Lys Asn Glu Val Ser Lys Pro Ala Glu
1               5                   10                  15

Val Gln Gly Lys Tyr Val Lys Lys Glu Thr Ser Pro Leu Leu Arg Asn
            20                  25                  30

Leu Met Pro Ser Phe Ile Arg His Gly Pro Thr Ile Pro Arg Arg Thr
        35                  40                  45

Asp Leu Cys Leu Pro Asp Ser Ser Ala Thr Ala Phe Ser Ala Ser Gly
    50                  55                  60

Asp Gly Val Val Ser Arg Asn Gln Ser Phe Leu Arg Thr Ala Ile Gln
65                  70                  75                  80

Arg Thr Pro His Glu Val Met Arg Arg Glu Ser His Arg Leu Ser Ala
                85                  90                  95

Pro Ser Tyr Leu Val Arg Ser Leu Ala Asp Val Pro Arg Glu Cys Gly
            100                 105                 110

Ser Ser Gln Ser Phe Leu Thr Glu Val Asn Phe Ala Val Glu Asn Gly
        115                 120                 125

Asp Ser Gly Ser Arg Tyr Phe Phe Ser Asp Asn Phe Phe Asp Gly Gln
    130                 135                 140

Arg Arg Arg Pro Leu Gly Asp Arg Ala Gln Glu Asp Tyr Arg Tyr Tyr
145                 150                 155                 160
```

```
Glu Tyr Asn His Asp Leu Phe Gln Arg Met Pro Gln Ser Gln Gly Arg
            165                 170                 175

His Thr Ser Gly Ile Gly Arg Val Thr Ala Thr Ser Leu Gly Asn Leu
            180                 185                 190

Thr Asn His Gly Ser Glu Asp Leu Pro Leu Pro Pro Gly Trp Ser Val
            195                 200                 205

Asp Trp Thr Met Arg Gly Arg Lys Tyr Tyr Ile Asp His Asn Thr Asn
        210                 215                 220

Thr Thr His Trp Ser His Pro Leu Glu Arg Glu Gly Leu Pro Pro Gly
225                 230                 235                 240

Trp Glu Arg Val Glu Ser Ser Glu Phe Gly Thr Tyr Tyr Val Asp His
                245                 250                 255

Thr Asn Lys Arg Ala Gln Tyr Arg His Pro Cys Ala Pro Ser Val Pro
            260                 265                 270

Arg Tyr Asp Gln Pro Pro Ile Thr Tyr Gln Pro Gln Gln Thr Glu
        275                 280                 285

Arg Asn Gln Ser Leu Leu Val Pro Ala Asn Pro Tyr His Thr Ala Glu
            290                 295                 300

Ile Pro Asp Trp Leu Gln Val Tyr Ala Arg Ala Pro Val Lys Tyr Asp
305                 310                 315                 320

His Ile Leu Lys Trp Glu Leu Phe Gln Leu Ala Asp Leu Asp Thr Tyr
                325                 330                 335

Gln Gly Met Leu Lys Leu Leu Phe Met Lys Glu Leu Glu Gln Ile Val
            340                 345                 350

Lys Leu Tyr Glu Ala Tyr Arg Gln Ala Leu Leu Thr Glu Leu Glu Asn
            355                 360                 365

Arg Lys Gln Arg Gln Trp Tyr Ala Gln Gln His Gly Lys Thr Phe
        370                 375                 380

Leu Ser
385

<210> SEQ ID NO 3
<211> LENGTH: 387
<212> TYPE: PRT
<213> ORGANISM: Artificial Sequence
<220> FEATURE:
<223> OTHER INFORMATION: amino acid sequence of rat WW45 protein

<400> SEQUENCE: 3

Met Leu Ser Arg Lys Lys Thr Lys Asn Glu Val Ser Lys Pro Ala Glu
  1               5                  10                  15

Val Gln Gly Lys Tyr Val Lys Lys Glu Thr Ser Pro Leu Leu Arg Asn
             20                  25                  30

Leu Met Pro Ser Phe Ile Arg His Gly Pro Thr Ile Pro Arg Arg Thr
            35                  40                  45

Asp Leu Cys Leu Pro Glu Ser Ser Ala Ser Ala Phe Ser Ala Ser Gly
     50                  55                  60

Asp Gly Val Val Ser Arg Asn Gln Ser Phe Leu Arg Thr Pro Val Gln
 65                  70                  75                  80

Arg Thr Pro His Glu Val Met Arg Arg Glu Ser Asn Arg Leu Ser Ala
                 85                  90                  95

Pro Ser Ser Tyr Leu Val Arg Ser Leu Ala Asp Val Pro Arg Glu Tyr
            100                 105                 110

Gly Ser Ser Gln Ser Phe Leu Thr Glu Val Asn Phe Ala Val Glu Asn
            115                 120                 125

Gly Asp Ser Gly Ser Arg Tyr Phe Tyr Ser Asp Asn Phe Phe Asp Gly
```

```
                    130                 135                 140
Gln Arg Arg Pro Leu Gly Asp Arg Ala Gln Glu Asp Tyr Arg Tyr
145                 150                 155                 160

Tyr Glu Tyr Asn His Asp Leu Phe Gln Arg Met Pro Gln Asn Gln Gly
                    165                 170                 175

Arg His Thr Ser Gly Ile Gly Arg Val Thr Ala Thr Ser Leu Gly Asn
                180                 185                 190

Leu Thr Asn His Gly Ser Glu Asp Leu Pro Leu Pro Pro Gly Trp Ser
                195                 200                 205

Val Asp Trp Thr Met Arg Gly Arg Lys Tyr Tyr Ile Asp His Asn Thr
210                 215                 220

Asn Thr Thr His Trp Ser His Pro Leu Glu Arg Glu Gly Leu Pro Pro
225                 230                 235                 240

Gly Trp Glu Arg Val Glu Ser Ser Glu Phe Gly Thr Tyr Tyr Val Asp
                245                 250                 255

His Thr Asn Lys Arg Ala Gln Tyr Arg His Pro Cys Ala Pro Ser Val
                260                 265                 270

Pro Arg Tyr Asp Gln Pro Pro Ile Thr Tyr Gln Pro Gln Gln Thr
                275                 280                 285

Glu Arg Asn Gln Ser Leu Leu Val Pro Ala Asn Pro Tyr His Thr Ala
290                 295                 300

Glu Ile Pro Asp Trp Leu Gln Val Tyr Ala Arg Ala Pro Val Lys Tyr
305                 310                 315                 320

Asp His Ile Leu Lys Trp Glu Leu Phe Gln Leu Ala Asp Leu Asp Thr
                325                 330                 335

Tyr Gln Gly Met Leu Lys Leu Leu Phe Met Lys Glu Leu Glu Gln Ile
                340                 345                 350

Val Lys Leu Tyr Glu Ala Tyr Arg Gln Ala Leu Val Thr Glu Leu Glu
                355                 360                 365

Asn Arg Lys Gln Arg Gln Gln Trp Tyr Ala Gln His His Gly Lys Lys
                370                 375                 380

Phe Leu Ser
385

<210> SEQ ID NO 4
<211> LENGTH: 454
<212> TYPE: PRT
<213> ORGANISM: Artificial Sequence
<220> FEATURE:
<223> OTHER INFORMATION: amino acid sequence of human YAP

<400> SEQUENCE: 4

Met Asp Pro Gly Gln Gln Pro Pro Gln Pro Ala Pro Gln Gly Gln
1               5                   10                  15

Gly Gln Pro Pro Ser Gln Pro Pro Gln Gly Gln Gly Pro Pro Ser Gly
                20                  25                  30

Pro Gly Gln Pro Ala Pro Ala Ala Thr Gln Ala Ala Pro Gln Ala Pro
                35                  40                  45

Pro Ala Gly His Gln Ile Val His Val Arg Gly Asp Ser Glu Thr Asp
            50                  55                  60

Leu Glu Ala Leu Phe Asn Ala Val Met Asn Pro Lys Thr Ala Asn Val
65                  70                  75                  80

Pro Gln Thr Val Pro Met Arg Leu Arg Lys Leu Pro Asp Ser Phe Phe
                85                  90                  95

Lys Pro Pro Glu Pro Lys Ser His Ser Arg Gln Ala Ser Thr Asp Ala
                100                 105                 110
```

```
Gly Thr Ala Gly Ala Leu Thr Pro Gln His Val Arg Ala His Ser Ser
            115                 120                 125

Pro Ala Ser Leu Gln Leu Gly Ala Val Ser Pro Gly Thr Leu Thr Pro
        130                 135                 140

Thr Gly Val Val Ser Gly Pro Ala Ala Thr Pro Thr Ala Gln His Leu
145                 150                 155                 160

Arg Gln Ser Ser Phe Glu Ile Pro Asp Asp Val Pro Leu Pro Ala Gly
                165                 170                 175

Trp Glu Met Ala Lys Thr Ser Ser Gly Gln Arg Tyr Phe Leu Asn His
            180                 185                 190

Ile Asp Gln Thr Thr Thr Trp Gln Asp Pro Arg Lys Ala Met Leu Ser
        195                 200                 205

Gln Met Asn Val Thr Ala Pro Thr Ser Pro Pro Val Gln Gln Asn Met
    210                 215                 220

Met Asn Ser Ala Ser Ala Met Asn Gln Arg Ile Ser Gln Ser Ala Pro
225                 230                 235                 240

Val Lys Gln Pro Pro Pro Leu Ala Pro Gln Ser Pro Gln Gly Gly Val
                245                 250                 255

Met Gly Gly Ser Asn Ser Asn Gln Gln Gln Met Arg Leu Gln Gln
            260                 265                 270

Leu Gln Met Glu Lys Glu Arg Leu Arg Leu Lys Gln Gln Glu Leu Leu
        275                 280                 285

Arg Gln Val Arg Pro Gln Glu Leu Ala Leu Arg Ser Gln Leu Pro Thr
    290                 295                 300

Leu Glu Gln Asp Gly Gly Thr Gln Asn Pro Val Ser Ser Pro Gly Met
305                 310                 315                 320

Ser Gln Glu Leu Arg Thr Met Thr Thr Asn Ser Ser Asp Pro Phe Leu
                325                 330                 335

Asn Ser Gly Thr Tyr His Ser Arg Asp Glu Ser Thr Asp Ser Gly Leu
            340                 345                 350

Ser Met Ser Ser Tyr Ser Val Pro Arg Thr Pro Asp Asp Phe Leu Asn
        355                 360                 365

Ser Val Asp Glu Met Asp Thr Gly Asp Thr Ile Asn Gln Ser Thr Leu
    370                 375                 380

Pro Ser Gln Gln Asn Arg Phe Pro Asp Tyr Leu Glu Ala Ile Pro Gly
385                 390                 395                 400

Thr Asn Val Asp Leu Gly Thr Leu Glu Gly Asp Gly Met Asn Ile Glu
                405                 410                 415

Gly Glu Glu Leu Met Pro Ser Leu Gln Glu Ala Leu Ser Ser Asp Ile
            420                 425                 430

Leu Asn Asp Met Glu Ser Val Leu Ala Ala Thr Lys Leu Asp Lys Glu
        435                 440                 445

Ser Phe Leu Thr Trp Leu
    450

<210> SEQ ID NO 5
<211> LENGTH: 472
<212> TYPE: PRT
<213> ORGANISM: Artificial Sequence
<220> FEATURE:
<223> OTHER INFORMATION: amino acid sequence of mouse YAP

<400> SEQUENCE: 5

Met Glu Pro Ala Gln Gln Pro Pro Pro Gln Pro Ala Pro Gln Gly Pro
  1               5                  10                  15
```

-continued

```
Ala Pro Pro Ser Val Ser Pro Ala Gly Thr Pro Ala Ala Pro Pro Ala
             20                  25                  30

Pro Pro Ala Gly His Gln Val His Val Arg Gly Asp Ser Glu Thr
         35                  40                  45

Asp Leu Glu Ala Leu Phe Asn Ala Val Met Asn Pro Lys Thr Ala Asn
             50                  55                  60

Val Pro Gln Thr Val Pro Met Arg Leu Arg Lys Leu Pro Asp Ser Phe
 65                  70                  75                  80

Phe Lys Pro Pro Glu Pro Lys Ser His Ser Arg Gln Ala Ser Thr Asp
                 85                  90                  95

Ala Gly Thr Ala Gly Ala Leu Thr Pro Gln His Val Arg Ala His Ser
             100                 105                 110

Ser Pro Ala Ser Leu Gln Leu Gly Ala Val Ser Pro Gly Thr Leu Thr
         115                 120                 125

Ala Ser Gly Val Val Ser Gly Pro Ala Ala Pro Ala Ala Gln His
         130                 135                 140

Leu Arg Gln Ser Ser Phe Glu Ile Pro Asp Asp Val Pro Leu Pro Ala
145                 150                 155                 160

Gly Trp Glu Met Ala Lys Thr Ser Ser Gly Gln Arg Tyr Phe Leu Asn
                 165                 170                 175

His Asn Asp Gln Thr Thr Thr Trp Gln Asp Pro Arg Lys Ala Met Leu
             180                 185                 190

Ser Gln Leu Asn Val Pro Ala Pro Ala Ser Pro Ala Val Pro Gln Thr
         195                 200                 205

Leu Met Asn Ser Ala Ser Gly Pro Leu Pro Asp Gly Trp Glu Gln Ala
         210                 215                 220

Met Thr Gln Asp Gly Glu Val Tyr Tyr Ile Asn His Lys Asn Lys Thr
225                 230                 235                 240

Thr Ser Trp Leu Asp Pro Arg Leu Asp Pro Arg Phe Ala Met Asn Gln
                 245                 250                 255

Arg Ile Thr Gln Ser Ala Pro Val Lys Gln Pro Pro Leu Ala Pro
             260                 265                 270

Gln Ser Pro Gln Gly Gly Val Leu Gly Gly Ser Ser Asn Gln Gln
         275                 280                 285

Gln Gln Ile Gln Leu Gln Gln Leu Gln Met Glu Lys Glu Arg Leu Arg
         290                 295                 300

Leu Lys Gln Gln Glu Leu Phe Arg Gln Glu Leu Ala Leu Arg Ser Gln
305                 310                 315                 320

Leu Pro Thr Leu Glu Gln Asp Gly Gly Thr Pro Asn Ala Val Ser Ser
                 325                 330                 335

Pro Gly Met Ser Gln Glu Leu Arg Thr Met Thr Thr Asn Ser Ser Asp
             340                 345                 350

Pro Phe Leu Asn Ser Gly Thr Tyr His Ser Arg Asp Glu Ser Thr Asp
         355                 360                 365

Ser Gly Leu Ser Met Ser Ser Tyr Ser Ile Pro Arg Thr Pro Asp Asp
         370                 375                 380

Phe Leu Asn Ser Val Asp Glu Met Asp Thr Gly Asp Thr Ile Ser Gln
385                 390                 395                 400

Ser Thr Leu Pro Ser Gln Gln Ser Arg Phe Pro Asp Tyr Leu Glu Ala
                 405                 410                 415

Leu Pro Gly Thr Asn Val Asp Leu Gly Thr Leu Glu Gly Asp Ala Met
             420                 425                 430

Asn Ile Glu Gly Glu Glu Leu Met Pro Ser Leu Gln Glu Ala Leu Ser
         435                 440                 445
```

Ser Glu Ile Leu Asp Val Glu Ser Val Leu Ala Ala Thr Lys Leu Asp
    450                 455                 460

Lys Glu Ser Phe Leu Thr Trp Leu
465                 470

<210> SEQ ID NO 6
<211> LENGTH: 366
<212> TYPE: PRT
<213> ORGANISM: Artificial Sequence
<220> FEATURE:
<223> OTHER INFORMATION: amino acid sequence of rat YAP

<400> SEQUENCE: 6

Met Glu Pro Ala Gln Pro Pro Gln Pro Ala Pro Gln Gly Pro
1               5                   10                  15

Ala Pro Pro Ser Val Ser Pro Ala Gly Thr Pro Ala Ala Pro Pro Ala
                20                  25                  30

Pro Pro Ala Gly His Gln Val Val His Val Arg Gly Asp Ser Glu Thr
            35                  40                  45

Asp Leu Glu Ala Leu Phe Asn Ala Val Met Asn Pro Lys Thr Ala Asn
    50                  55                  60

Val Pro Gln Thr Val Pro Met Arg Leu Arg Lys Leu Pro Asp Ser Phe
65                  70                  75                  80

Phe Lys Pro Pro Glu Pro Lys Ser His Ser Arg Gln Ala Ser Thr Asp
                85                  90                  95

Ala Gly Thr Ala Gly Ala Leu Thr Pro Gln His Val Arg Ala His Ser
            100                 105                 110

Ser Pro Ala Ser Leu Gln Leu Gly Ala Gly Thr Leu Thr Ala Ser Gly
    115                 120                 125

Val Val Ser Gly Pro Ala Ala Thr Pro Ala Ala Gln His Leu Arg Gln
130                 135                 140

Ser Ser Phe Glu Ile Pro Asp Asp Val Pro Leu Pro Ala Gly Trp Glu
145                 150                 155                 160

Met Ala Lys Thr Ser Ser Gly Gln Arg Tyr Phe Leu Asn His Asn Asp
                165                 170                 175

Gln Thr Thr Thr Trp Gln Asp Pro Arg Lys Ala Met Leu Ser Gln Leu
            180                 185                 190

Asn Val Pro Thr Ser Ala Ser Pro Ala Val Pro Gln Thr Leu Met Asn
    195                 200                 205

Ser Ala Ser Gly Pro Leu Pro Asp Gly Trp Glu Gln Ala Met Thr Gln
210                 215                 220

Asp Gly Glu Val Tyr Tyr Ile Asn His Lys Asn Lys Thr Thr Ser Trp
225                 230                 235                 240

Leu Asp Pro Arg Leu Asp Pro Arg Phe Ala Met Asn Gln Arg Ile Thr
                245                 250                 255

Gln Ser Ala Pro Val Lys Gln Pro Pro Leu Ala Pro Gln Ser Pro
            260                 265                 270

Gln Gly Gly Val Leu Gly Gly Ser Ser Asn Gln Gln Gln Ile
    275                 280                 285

Gln Leu Gln Gln Leu Gln Met Glu Lys Glu Arg Leu Arg Leu Lys Gln
    290                 295                 300

Gln Glu Leu Phe Arg Gln Ala Ile Arg Asn Ile Asn Pro Ser Thr Ala
305                 310                 315                 320

Asn Ala Pro Lys Cys Gln Thr Val Arg Ala Gly Ile Ser Ser Pro Gln
                325                 330                 335

Pro Val Ala Leu Thr Gly Ala Gly Trp Arg Asp Ser Glu Cys Ser Val
     340                 345                 350

Phe Ser Arg Asp Asp Ser Gly Ile Glu Asp Asn Asp Asn Gln
        355                 360                 365

<210> SEQ ID NO 7
<211> LENGTH: 3031
<212> TYPE: DNA
<213> ORGANISM: Artificial Sequence
<220> FEATURE:
<223> OTHER INFORMATION: gene for human WW45 protein

<400> SEQUENCE: 7

| | | | | | | |
|---|---|---|---|---|---|---|
| gtggtagcgg | ttattcggcg | gcccgcggcg | gaccatggcc | ctggccctgg | cccggcgtcg | 60 |
| ctgggctttc | ctcacggcgt | ccccgagcag | cgtcgcagag | cgggccgact | tccgggaagg | 120 |
| aactgaccag | cgactgagcg | gcggccggcg | cgcttagcgc | cctgaacatg | cggcagtccc | 180 |
| tgcgggcgac | cccgggctcc | ggacaggcgg | cggcggaggc | ggcggctcgg | gagggaagga | 240 |
| ggcggcggcg | ccggcggagg | tggcggcgga | gacggccggc | gccggcgcg | gagccctagg | 300 |
| gaggcagttc | agcgcggcct | cgggcctcgt | cgagaaggat | gctgtcccga | agaaaaccca | 360 |
| aaaacgaagt | gtccaagccg | gccgaggtgc | agggaagta | cgtgaagaag | gagacgtcgc | 420 |
| ctctgcttcg | gaatcttatg | ccttcattca | tccggcatgg | tccaacaatt | ccaagacgaa | 480 |
| ctgatatctg | tcttccagat | tcaagcccta | atgccttttc | aacttctgga | gatgtagttt | 540 |
| caagaaacca | gagtttcctt | agaactccaa | ttcaaagaac | acctcatgaa | ataatgagaa | 600 |
| gagaaagcaa | cagattatct | gcaccttctt | atcttgccag | aagtctagca | gatgtcccta | 660 |
| gagagtatgg | ttcttctcag | tcatttgtaa | cggaagttag | ttttgctgtt | gaaaatggag | 720 |
| actctggttc | ccgatattat | tattcagaca | attttttga | tggtcagaga | aagcggccac | 780 |
| ttggagatcg | tgcacatgaa | gactacagat | attatgaata | caaccatgat | ctcttccaaa | 840 |
| gaatgccaca | gaatcagggg | aggcatgctt | caggtattgg | gagagttgct | gctacatctt | 900 |
| taggaaattt | gactaaccat | ggttctgaag | atttaccccct | tcctcctggc | tggtctgtgg | 960 |
| actgacaat | gagagggaga | aaatattata | tagatcataa | cacaaataca | actcactgga | 1020 |
| gccatcctct | tgagcgagaa | ggacttcctc | ctggatggga | acgagttgag | tcatccgaat | 1080 |
| ttggaaccta | ttatgtagat | cacacaaata | agaaggccca | atacaggcat | ccctgtgctc | 1140 |
| ctagtgtacc | tcggtatgat | caaccacctc | ctgtcacata | ccagccacag | caaactgaaa | 1200 |
| gaaatcagtc | ccttctggta | cctgcaaatc | catatcatac | tgcagaaatt | cctgactggc | 1260 |
| ttcaggttta | cgcacgagcc | cctgtgaaat | atgaccacat | tctgaagtgg | gaactcttcc | 1320 |
| agctggctga | cctggataca | taccagggaa | tgctaaagtt | gctcttcatg | aaagaattgg | 1380 |
| agcagattgt | taaatgtat | gaagcataca | gacaagccct | tcttacagag | ttggaaaacc | 1440 |
| gaaagcagag | acagcagtgg | tatgcccaac | aacatggaaa | aaattttga | gctgattttt | 1500 |
| taaaaattta | agttttgtaa | gagctttaaa | atattttcac | agataaaaaa | ttgcaaacaa | 1560 |
| gtactctggt | taataaatgc | tgcttccttt | gtggaaatta | taaaattcta | actttacatg | 1620 |
| tattttgtta | ttagaaattt | tcttttattg | aatgagaaaa | attagtctat | cattttaaga | 1680 |
| gccaatatgg | caaacacttt | caaatactgt | atattaggaa | actgttttgg | tattcttgat | 1740 |
| ggaaaaaaac | gcagcggaaa | tgtcattatg | aacagatgtt | aaataggaaa | ttattacttg | 1800 |
| ttaacttctt | acagcagtag | taccttcttt | aaaaaaaaaa | aagaatctgc | ggtatttttt | 1860 |
| taaaaaaaaa | gtttaccgct | gtagtgtgaa | atattgtctg | gaaagggatg | gtttaaatat | 1920 |

| | |
|---|---|
| taccatgatg tagttgaaat ataaaatagg atttggaacc ttattgtgat aaatatttat | 1980 |
| atatgatgta tgtttgtctc ccctctccaa agtaaggaac ccagctgggc gtggtggctc | 2040 |
| actcctgtaa tcccagcatt ttgggaggcc gaggtgggtg gaccgcttga gtccacgagt | 2100 |
| ttaagaccag cctgggcaac atggtgaagc cccatctcta caaaaaatac aaaaaaatta | 2160 |
| gccgggtatg atggtgtgtg cctctagtcc cagctacttg ggaggctgag gtcagaggat | 2220 |
| ggcttgagcc caagaggcag aggttgcagg gtcaagatcg caccacttgc actgcagcct | 2280 |
| gagagagaga gagccagacc ttgtctcaaa aaataaaaaa taaaaaaata aaacaaaat | 2340 |
| aaggaatcct tttaaagcat gttgagaaag tattttttgg tatgaatggg tgacgggcct | 2400 |
| tttaatcttt caggaataca tataagcagg aatacttagc ctgtattggg aaggtgcgtg | 2460 |
| aaactcaaag ttgctaacat catcttcctt attttcagcc agtgctgtta ctgcatttag | 2520 |
| catggctctg acgaggcagt ggagagttcc tgacagcata gcatactgcc ttctgacaga | 2580 |
| ctgggttaag ctaccaaaaa tgacaaccag ggattcaaaa aaaattttg gtcattaaat | 2640 |
| cgaatgtata ttattacttt ttaattttct aagtatttat cacaggactt taacaccata | 2700 |
| tatttccctc ccagtttttc tcccttttg gtttaatagt taaaacattt ttcataatta | 2760 |
| gtgctgtaca tttgattgca aacaaattgg tgatacttct aaactataac tataaatctc | 2820 |
| tagaattctg tgaatttcaa cattatttga agtagttctt cagttatatt tacatgtgtt | 2880 |
| gtaaatatgt aaatatactt ttagcttagg aagtcttcca gaatacaaac tactcccagt | 2940 |
| tagatatcag tgagtttgaa taactgaaga aatgttgaca atgttaagtg tttgatttta | 3000 |
| tataacaagc ttattaaata tattttgtg g | 3031 |

<210> SEQ ID NO 8
<211> LENGTH: 2524
<212> TYPE: DNA
<213> ORGANISM: Artificial Sequence
<220> FEATURE:
<223> OTHER INFORMATION: gene for mouse WW45 protein

<400> SEQUENCE: 8

| | |
|---|---|
| caaggcggcc tcgggcggcg tcgttgagcc ggctgacttc ccgggaggag ctgccctgcg | 60 |
| actgagcggc ggcgggcgcg cttagcgcgg ccaacatgcg gcggagcctg cgggcgggcg | 120 |
| cgggcggcgg agacccgagg cgaaggcggc ggcggcggcc cggagggcgg cggcgggcgg | 180 |
| caggctcgcg gccctagcga ggctgctggg gcggcggcgg gagtcgtccg cgaggatgct | 240 |
| gtcccgcaag aaaaccaaaa acgaggtgtc taagccggcc gaggtgcagg gcaagtacgt | 300 |
| gaagaaggag acgtcgcccc tgctgcggaa tctcatgcct tcattcattc ggcacggtcc | 360 |
| aacaattccc agacggactg acctctgtct tccagattca agtgctactg ctttctcagc | 420 |
| ttctggagat ggtgtagttt caagaaacca gagtttcctg agaactgcaa ttcaaaggac | 480 |
| acctcatgaa gtaatgagaa gagaaagcca cagactgtct gccccttctt accttgtcag | 540 |
| gagcctagca gatgtccctc gagagtgtgg ctcatcacag tcattttga cagaagttaa | 600 |
| ctttgctgtt gagaatggag actctggctc ccgatacttc ttctcagata actttttga | 660 |
| tggacagaga aggcggccac ttggagatcg tgcacaagaa gattacagat attatgaata | 720 |
| caaccatgat ctcttccaga ggatgccaca gagtcagggg aggcacactt caggtattgg | 780 |
| gagagtcacg gctacatctc tagggaattt aactaaccat ggatctgaag atttacccct | 840 |
| tcctcctggc tggtctgtgg actggacaat gagagggaga aaatactaca tagatcataa | 900 |
| cacaaatacc actcactgga gtcatcccct tgaacgagaa ggacttcctc ctggctggga | 960 |

```
acgagtagag tcatcagaat ttggaaccta ttacgtggat cacaccaata aaagggctca   1020
gtacaggcac ccctgtgctc cgagtgtacc tcggtatgat cagcctccac ccatcacgta   1080
tcagccacaa caaactgaaa gaaatcagtc tctcctggtc cctgcaaatc cctaccatac   1140
tgcagaaatt cctgactggc ttcaggttta tgcccgagcc cctgtgaaat atgaccacat   1200
tctgaagtgg gagctcttcc agctggctga cctggacacg taccagggaa tgctgaagtt   1260
gctcttcatg aaggaactgg agcagattgt gaagttgtac gaggcctaca gacaggctct   1320
tctcactgag ttggaaaacc gcaagcagag gcagcagtgg tatgcccagc agcatggcaa   1380
gacgttctta agtaacttaa tcacaagcca agtttataag agctttaaaa tattttcaga   1440
taaatgactg caaacaagtt ctttggttaa taaaggtaac ttactatttg gaagtataaa   1500
attctagttt tacatatatt ttgttatcaa ttttttttct tttattgaac caagaaagtt   1560
ttatcattta aaaagccaat atggcatatg ctaccaaatg ctgtattagg aaactgctgg   1620
agactctgga caaaaagtag tacaggaaga gattatcagc ataaacaggc attaaatagg   1680
aaaccgtcac tctctgactt tttatggaca cacccttctt gtttaggaaa cagaagagga   1740
tgagagtaca tctgtgatca gttgctacgt gtggtgtcaa gtgttttctg gaatgagatg   1800
gtttgactat taccataggt atagttcaaa atacaaaaca ggacttggaa cctttattgt   1860
aacaagcttg tacgtgtgtg gtcatctccc ccccgccccc tcagtccccc gaccccccaat   1920 gtaaggaaca ccttttgaagg agaaagatga agtctttgag gaatacattc agaaatacag   1980
gactataata aatacatgcc tcttagtgcg caactgttgc taatacggct tccttccttt   2040
gaggcagagc acataagtac agttagcatg gctctgagac acagcacagg cttcctgacc   2100
acatagaata ctgccttcca tcagggtggg ctaagttgcc aaaaacgaca atcagggatc   2160
caataagcaa tcttggtcac ttaagtaaat tttatattgc cttttttatc tttgagaagt   2220
atttgtcata aaggtgtaga aacaggctgt cattccttcc tattttttctt gctttgggtt   2280 taatagttgt tcataattag tgctgaacac ttgattacag ataaacttat ggaacttcca   2340
gctgtaaatc tagaattctt gagcttcata gctcttcagt tgtgcttaca aatgttgtga   2400
atatgtatat atattagttc ttttcctaag tataagcact ccatgttaga agtgactttg   2460
aattattgat aaaatttcgc atttgatttt ataacaag ttattaaata tattttgtg    2520 gaaa                                                                2524
```

```
<210> SEQ ID NO 9
<211> LENGTH: 2047
<212> TYPE: DNA
<213> ORGANISM: Artificial Sequence
<220> FEATURE:
<223> OTHER INFORMATION: gene for rat WW45 protein

<400> SEQUENCE: 9
```

```
gtgagcggcg gcgggcgcgc ttagcgccgc caacatgcgg cggagcctgc gggcgggcgc     60
gggcggcgga gacccgaggc gaaggcggcg ccggcccggg aggcggcggc gggcggcggg    120
ctcgcggccc tagcgaggct gctggggcag cggcgggcga cgtccgcgag gatgctgtcc    180
cgcaagaaaa ccaaaaacga ggtgtctaag ccggccgagg ttcagggcaa gtacgtgaag    240
aaggagacgt cgcccctgct gcggaatctc atgccttcat tcattcggca cggtccaaca    300
attccaagac ggactgacct ctgtcttcca gagtcaagcg ctagtgcttt ctcagcttct    360
ggagatggcg tagtttcaag aaaccagagt ttcctgagaa ctccagttca aggacgcct    420 catgaagtaa tgagaagaga aagcaacaga ctgtccgcac cgtcttctta ccttgtcagg    480
```

```
agcctagcgg atgtccctcg ggaatacggc tcatcacagt cattttaac agaagttaat    540 tttgctgttg aaaatggaga ctctggttcc cgatattttt attcagataa ctttttgat     600 ggtcagagaa ggaggccact tggagatcgt gcacaagaag actatagata ttatgaatac    660
aaccatgatc tcttccaaag aatgccacag aatcagggga ggcacacatc aggtattggg    720
agagtcactg ctacatcttt aggaaattta actaaccatg gatctgaaga tttaccccett   780 cctcctggct ggtctgtgga ctggacaatg agagggagaa atactacat agatcataac     840 acaaacacaa ctcattggag tcatcctctt gaacgagaag acttcctcc tgggtgggag     900 cgagtggaat catcagaatt tggaacctat tatgtggatc acacaaataa aagggctcag    960
tacaggcacc cctgtgctcc cagtgtgcct cggtatgatc agcctccacc catcacgtat   1020
cagccacagc aaactgaaag aaatcagtct ctcctggtcc ctgcaaaccc ctaccatact   1080
gcagaaattc ctgactggct tcaggtttat gcccgagccc ctgtgaaata cgaccacatt   1140
ctgaagtggg agctcttcca gctggctgac ctggacacgt accagggaat gctgaagctg   1200
ctcttcatga aggagctgga gcagattgtc aagttgtatg aggcctacag acaggctctt   1260
gtcaccgagc tggaaaaccg caagcagagg cagcagtggg atgcccagca ccatggcaag   1320 aagttttaa gttaactttc cacaagccag gttttgtaag agctttaaaa tattttcaga    1380
taaatgactg caaacaagtt ctttggttaa taaaggcaac ttactattttg gaattacaaa   1440 attctagttt tacatatatt atcaactttt tcttttattg aaccaagaaa gttttatcac   1500
ttaaaaagcc aatatggcat atactaccaa atgctgttag gaaactgctt tggagactgt   1560
ggatggaaag gagtacagga agagactgtc ataaatggca ttaaacagga gtggacacac   1620
ccttcttgtt ccgaaaagga agcggacgag agcacactgt gaacagcggc tccttgtggt   1680
gtcaggtgtt ttctggaatg agatggtgtg accattgcca tgggtatagt tcagaataaa   1740
aacagggcat ggagccttta tggggacaaa cgtgtatatg gtgtgtgtgg tcatctactc   1800
ccacctcctc cctatgtgag ggacacctttt gaaggaggga gataaagcct ttcaggaata   1860
gagtcaggaa tacgggaata taataaatac gggcctcagt tggtgcgaaa ctgttgctaa   1920
tactgcttcc ttccttcctt tgagccgag cacatgagta cagtcagcaa ggctctggtg    1980
agacacagca cgggcttcct gaccacaggg aatactgtct tccatcaggc tgggctacgt   2040
gccaaaa                                                              2047

<210> SEQ ID NO 10
<211> LENGTH: 48
<212> TYPE: PRT
<213> ORGANISM: Artificial Sequence
<220> FEATURE:
<223> OTHER INFORMATION: SARAH domain of human WW46

<400> SEQUENCE: 10

Ile Leu Lys Trp Glu Leu Phe Gln Leu Ala Asp Leu Asp Thr Tyr Gln
 1               5                  10                  15

Gly Met Leu Lys Leu Leu Phe Met Lys Glu Leu Glu Gln Ile Val Lys
                20                  25                  30

Met Tyr Glu Ala Tyr Arg Gln Ala Leu Leu Thr Glu Leu Glu Asn Arg
            35                  40                  45

<210> SEQ ID NO 11
<211> LENGTH: 48
<212> TYPE: PRT
<213> ORGANISM: Artificial Sequence
<220> FEATURE:
<223> OTHER INFORMATION: SARAH domain of mouse WW45 protein
```

```
<400> SEQUENCE: 11

Ile Leu Lys Trp Glu Leu Phe Gln Leu Ala Asp Leu Asp Thr Tyr Gln
 1               5                  10                  15

Gly Met Leu Lys Leu Leu Phe Met Lys Glu Leu Glu Gln Ile Val Lys
            20                  25                  30

Leu Tyr Glu Ala Tyr Arg Gln Ala Leu Leu Thr Glu Leu Glu Asn Arg
        35                  40                  45

<210> SEQ ID NO 12
<211> LENGTH: 48
<212> TYPE: PRT
<213> ORGANISM: Artificial Sequence
<220> FEATURE:
<223> OTHER INFORMATION: SARAH domain of rat WW45 protein

<400> SEQUENCE: 12

Ile Leu Lys Trp Glu Leu Phe Gln Leu Ala Asp Leu Asp Thr Tyr Gln
 1               5                  10                  15

Gly Met Leu Lys Leu Leu Phe Met Lys Glu Leu Glu Gln Ile Val Lys
            20                  25                  30

Leu Tyr Glu Ala Tyr Arg Gln Ala Leu Val Thr Glu Leu Glu Asn Arg
        35                  40                  45

<210> SEQ ID NO 13
<211> LENGTH: 20
<212> TYPE: DNA
<213> ORGANISM: Artificial Sequence
<220> FEATURE:
<223> OTHER INFORMATION: WW45-L primer

<400> SEQUENCE: 13
tgaccatgtg tccagcctta                                           20

<210> SEQ ID NO 14
<211> LENGTH: 20
<212> TYPE: DNA
<213> ORGANISM: Artificial Sequence
<220> FEATURE:
<223> OTHER INFORMATION: WW$5-R primer

<400> SEQUENCE: 14
cgaatggatg ctgcatattg                                           20

<210> SEQ ID NO 15
<211> LENGTH: 25
<212> TYPE: DNA
<213> ORGANISM: Artificial Sequence
<220> FEATURE:
<223> OTHER INFORMATION: pGK-3 primer

<400> SEQUENCE: 15
gcacgagact agtgagacgt gctac                                     25

<210> SEQ ID NO 16
<211> LENGTH: 14
<212> TYPE: PRT
<213> ORGANISM: Artificial Sequence
<220> FEATURE:
<223> OTHER INFORMATION: antigen: 14 amino acids at C-terminus of mouse
      WW45 protein

<400> SEQUENCE: 16

Arg Lys Gln Arg Gln Gln Trp Tyr Ala Gln Gln His Gly Lys
 1               5                  10
```

```
<210> SEQ ID NO 17
<211> LENGTH: 21
<212> TYPE: DNA
<213> ORGANISM: Artificial Sequence
<220> FEATURE:
<223> OTHER INFORMATION: Sp-1 probe

<400> SEQUENCE: 17
cctagaccct ttcaacaagc a                                              21

<210> SEQ ID NO 18
<211> LENGTH: 20
<212> TYPE: DNA
<213> ORGANISM: Artificial Sequence
<220> FEATURE:
<223> OTHER INFORMATION: Sp-r probe

<400> SEQUENCE: 18
tgctatcact catcgggatt                                                20

<210> SEQ ID NO 19
<211> LENGTH: 17
<212> TYPE: PRT
<213> ORGANISM: Artificial Sequence
<220> FEATURE:
<223> OTHER INFORMATION: partial alignment of the conserved regions of
      Drosophila Yki

<400> SEQUENCE: 19

Leu Ala Ile His His Ser Arg Ala Arg Ser Ser Pro Ala Ser Leu Gln
 1               5                  10                  15

Gln

<210> SEQ ID NO 20
<211> LENGTH: 17
<212> TYPE: PRT
<213> ORGANISM: Artificial Sequence
<220> FEATURE:
<223> OTHER INFORMATION: partial alignment of the conserved regions of
      YAP

<400> SEQUENCE: 20

Leu Thr Pro Gln His Val Arg Ala His Ser Ser Pro Ala Ser Leu Gln
 1               5                  10                  15

Leu
```